US012209078B2

(12) United States Patent
Jiménez Cruz et al.

(10) Patent No.: US 12,209,078 B2
(45) Date of Patent: Jan. 28, 2025

(54) CRYSTALLINE FORMS OF CARBAZOLE INHIBITORS OF RhoGTPase FOR THE TREATMENT OF DISEASE

(71) Applicant: MBQ Pharma, Canovanas, PR (US)

(72) Inventors: Jocelyn M. Jiménez Cruz, San Sebastián, PR (US); Vilmalí López-Mejías, San Juan, PR (US); Torsten Stelzer, San Juan, PR (US)

(73) Assignee: MBQ Pharma, Canovanas, PR (US)

( * ) Notice: Subject to any disclaimer, the term of this patent is extended or adjusted under 35 U.S.C. 154(b) by 146 days.

(21) Appl. No.: 17/938,091

(22) Filed: Oct. 5, 2022

(65) Prior Publication Data

US 2023/0303529 A1 Sep. 28, 2023

Related U.S. Application Data

(60) Provisional application No. 63/252,801, filed on Oct. 6, 2021.

(51) Int. Cl.
 *C07D 403/04* (2006.01)
 *A61P 35/00* (2006.01)
(52) U.S. Cl.
 CPC ............ *C07D 403/04* (2013.01); *A61P 35/00* (2018.01); *C07B 2200/13* (2013.01)
(58) Field of Classification Search
 CPC .... C07D 403/04; A61P 35/00; C07B 2200/13
 See application file for complete search history.

(56) References Cited

U.S. PATENT DOCUMENTS

| | | | |
|---|---|---|---|
| 9,433,663 B2 | 9/2016 | Zheng | |
| 9,616,064 B2 | 4/2017 | Lawrence | |
| 2009/0082340 A1 | 3/2009 | Metz, Jr. | |
| 2010/0143474 A1 | 6/2010 | Rommelspacher | |
| 2023/0126139 A1 | 4/2023 | McCall | |

FOREIGN PATENT DOCUMENTS

| | | |
|---|---|---|
| WO | 1997011695 | 4/1997 |
| WO | 2022006377 | 1/2022 |

OTHER PUBLICATIONS

JimÃ© nez Cruz et al., Solubility Measurements and Correlation of MBQ-167 in Neat and Binary Solvent Mixtures, J. Chem. Eng. Data, 66, pp. 832â839 (Year: 2021).*
Khoshkhoo et al., Crystallization of polymorphs: the effect I of solvent, J. Phys. D Appl. Phys., 26, pp. B90-B93 (Year: 1993).*
Humphries-Bickley et al., Characterization of a Dual Rac/Cdc42 Inhibitor MBQ-167 in Metastatic Cancer, Mol. Canc. Therapeut., 16, pp. 805-818 (Year: 2017).*

(Continued)

*Primary Examiner* — Jeffrey S Lundgren
*Assistant Examiner* — Alexander K. Showalter
(74) *Attorney, Agent, or Firm* — Global Patent Group Inc.; Cynthia Hathaway; Brock Levin

(57) ABSTRACT

Disclosed herein are crystalline forms of compounds for the inhibition of RhoGTPase. Also disclosed herein are compounds, pharmaceutical compositions, and methods of treatment of RhoGTPase-mediated diseases, such as hyperproliferative and neoplastic diseases.

15 Claims, 11 Drawing Sheets

(56) References Cited

OTHER PUBLICATIONS

Jimenez Cruz et al., Solubility Measurements and Correlation of MBQ-167 in Neat and Binary Solvent Mixtures, J. Chem. Eng. Data, 66, pp. 832-839 (Year: 2021).*
International Application No. PCT/US2021/040055; International Preliminary Report on Patentability, date of issuance Jan. 12, 2023; 7 pages.
International Application No. PCT/US2021/040055; International Search Report and Written Opinion of the International Searching Authority, date of mailing Dec. 16, 2021; 10 pages.
Jiménez, J. et al., "Polymorphism in early development: The account of MBQ-167", Int J Pharm., 608:121064, 7 pages, (2021).
Jiménez, J. et al., "Solubility Measurements and Correlation of MBQ-167 in Neat and Binary Solvent Mixtures", J Chem Engin Data, 8 pages, (2020).
PubChem-SID: 386950363 Deposit Date: Nov. 4, 2019 (Nov. 4, 2019) pp. 1-7: p. 2.
U.S. Appl. No. 18/069,622; Application as filed, dated Dec. 21, 2022; 57 pages.

* cited by examiner

CRYSTALLINE FORMS OF CARBAZOLE INHIBITORS OF RhoGTPase FOR THE TREATMENT OF DISEASE This application claims the benefit of U.S. Provisional Application No. 63/252,801, filed Oct. 6, 2021, the entirety of which is hereby incorporated by reference as if written herein in its entirety.

Compounds are disclosed that inhibit Rho GTPases that are useful for inhibiting hyperproliferative and neoplastic diseases. Specifically, the compounds inhibit the GTPases Rac and Cdc42 that are overactive or overexpressed in signaling pathways in cancer and metastasis. Methods for treatment of cancer and hyperproliferative diseases are disclosed.

The Rho GTPases Rac (Ras-related C3 botulinum toxin substrate) and Cdc42 (cell division control protein 42 homolog) regulate cell functions governing cancer malignancy, including cell polarity, migration, and cell cycle progression. The Rho family of GTPases in humans consists of 20 different members, and aberrant behavior in their regulatory activity has been implicated in cancer and other diseases. More than 70 Guanine nucleotide Exchange Factors (GEFs) are known, which specifically activate one or more of the GTPases. In turn, the activated GTPases can specifically interact with over 60 downstream effectors. Dysregulation of one or more cellular processes can lead to release of malignant cells from their original locations, which subsequently can establish themselves in pre-metastatic niches in, for example, bone or lungs. It has been found that members of the Rho GTPase family, including Rac, Cdc42 and Rho, play key signaling roles in these processes.

Rho GTPases regulate migration and invasion, cytoskeletal organization, transcriptional regulation, cell cycle progression, apoptosis, vesicle trafficking, and cell-to-cell and cell-to-extracellular matrix adhesions. The Rho GTPases Rac and Cdc42 are potent inducers of actin polymerization and extension of actin structures at the leading edge of motile cells. In addition, Cdc42 plays a critical role in cell polarity, and thus, promotes directed and persistent migration.

Studies have implicated hyperactive Rac and Cdc42 with increased cancer cell survival, proliferation, and invasion, as well in Ras and other oncogene-mediated transformation. Furthermore, oncogenic cell surface receptors, such as tyrosine kinase, cytokine, and G protein coupled receptors, activate Rac and Cdc42 via regulation of their upstream effector GEFs. Accordingly, Rac and Cdc42 proteins are generally not mutated in cancer but rather overexpressed or hyperactivated. Even though ~9% of melanomas contain an activating Rac(P29S) mutation, and the hyperactive splice variant Rac1b is overexpressed in some cancers, a majority of the Rac and Cdc42 in human cancer are activated due to upregulated GEFs.

Of the direct downstream effectors of Rac and Cdc42, p21-activated kinases (PAK) are overexpressed in a number of cancers and contribute to cancer transformation and progression by regulating key cellular functions, including cytoskeletal organization, cell migration, adhesion, growth, and development. Therefore, a number of PAK inhibitors have been developed as anti-cancer therapeutics. However, these have been limited by specificity, bioavailability, and toxicity, and have yet to successfully complete clinical trials.

There is a need for new therapeutic agents for the treatment of cancer and other hyperproliferative diseases. The Rac and Cdc42 GTPases are important cellular mediators that are hyperactive or overexpressed in metastatic tumors. Design of novel inhibitors of the activities of Rac and/or Cdc42 with improved activity, pharmacochemical profile and reduced toxicity is desirable.

Disclosed herein are crystalline forms of compounds for the inhibition of GTPase. Also disclosed herein are pharmaceutical compositions comprising the crystalline forms. Also disclosed herein are methods for the treatment of RhoGTPase-mediated diseases, the methods comprising administration of a pharmaceutical composition comprising a crystalline form as disclosed herein, to a patient in need thereof.

DETAILED DESCRIPTION

Figure 1:
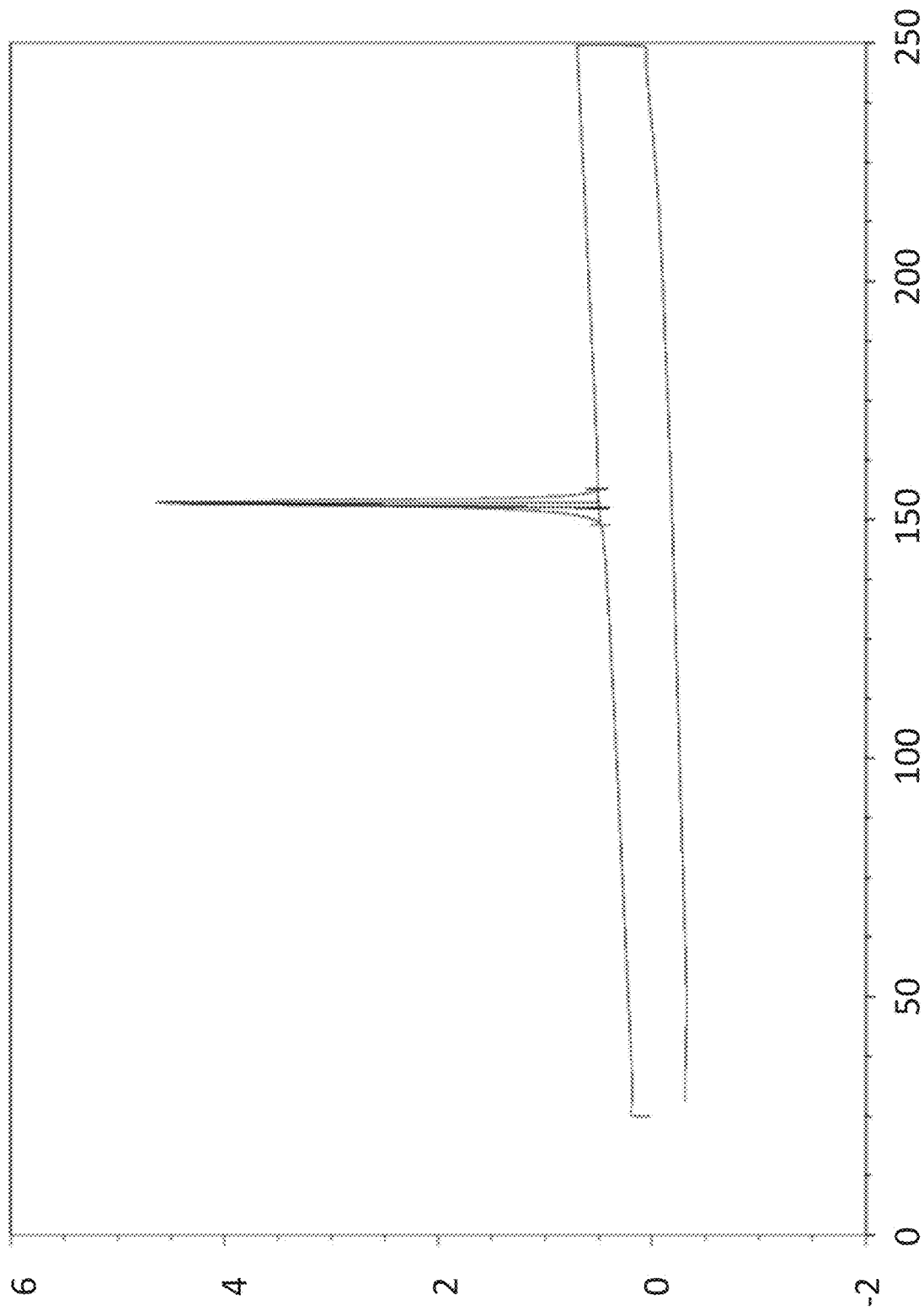
FIG. 1 shows a DSC thermograph of the Form I polymorph. Horizontal axis=temp (C); vertical axis=heat flow (mW).

Provided herein is Embodiment 1: a crystalline form of the compound 9-ethyl-3-(5-phenyl-1H-1,2,3-triazol-1-yl)-9H-carbazole, also known as MBQ-167:

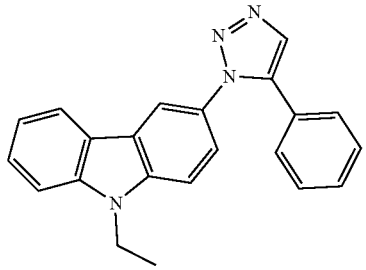 [SMILES: CCn1c2ccccc2c2cc(-n3nncc3-c3ccccc3)ccc21]

Embodiment 2: Polymorph I of the crystalline form of Embodiment 1.

Embodiment 3: The polymorph of Embodiment 2 having one or more PXRD peaks chosen from about 12.98, about 13.47, about 16.36, about 18.37, about 19.07, about 21.61, about 23.18, about 24.06, about 25.20, and about 30.62 degrees 2-theta.

Embodiment 4: The polymorph of Embodiment 3 having three or more of the peaks.

Embodiment 5: The polymorph of Embodiment 4 having five or more of the peaks.

Embodiment 6: The polymorph of Embodiment 5 having seven or more of the peaks.

Embodiment 7: The polymorph of Embodiment 6 having nine or more of the peaks.

Embodiment 8: The polymorph of Embodiment 2 having one or more PXRD peaks chosen from about 13.17, about 13.66, about 18.68, about 19.27, about 20.23, about 21.86, about 23.37, about 24.18, about 24.37, and about 25.52 degrees 2-theta.

Embodiment 9: The polymorph of Embodiment 8 having three or more of the peaks.

Embodiment 10: The polymorph of Embodiment 9 having five or more of the peaks.

Embodiment 11: The polymorph of Embodiment 10 having seven or more of the peaks.

Embodiment 12: The polymorph of Embodiment 11 having nine or more of the peaks.

Embodiment 13: Polymorph II of the crystalline form of Embodiment 1.

Embodiment 14: The polymorph of Embodiment 13 having one or more PXRD peaks chosen from about 12.20, about 14.54, about 15.78, about 18.22, about 20.61, about 21.90, about 25.94, about 26.32, about 28.17, and about 31.49 degrees 2-theta.

Embodiment 15: The polymorph of Embodiment 14 having three or more of the peaks.

Embodiment 16: The polymorph of Embodiment 15 having five or more of the peaks.

Embodiment 17: The polymorph of Embodiment 16 having seven or more of the peaks.

Embodiment 18: The polymorph of Embodiment 17 having nine or more of the peaks.

Embodiment 19: The polymorph of Embodiment 13 having one or more PXRD peaks chosen from about 12.35, about 14.60, about 15.97, about 18.39, about 18.54, about 19.76, about 20.87, about 22.03, about 26.48, and about 26.68 degrees 2-theta.

Embodiment 20: The polymorph of Embodiment 19 having three or more of the peaks.

Embodiment 21: The polymorph of Embodiment 20 having five or more of the peaks.

Embodiment 22: The polymorph of Embodiment 21 having seven or more of the peaks.

Embodiment 23: The polymorph of Embodiment 22 having nine or more of the peaks.

Embodiment 24: A method of treating a disease in a patient, the method comprising administering to the patient in need thereof an effective amount of a compound according to any one of Embodiments 1-23.

Embodiment 25. The method of Embodiment 24, wherein the disease is cancer.

Embodiment 26. The method of Embodiment 25, wherein the compound inhibits cancer cell migration.

Embodiment 27. The method of either one of Embodiments 25 and 26, wherein the cancer is selected from the group consisting of breast cancer, pancreatic cancer, ovarian cancer, gastric cancer, and neuronal cancer.

Embodiment 28. The method of Embodiment 27, wherein the cancer is pancreatic cancer.

Embodiment 29. The method of Embodiment 27, wherein the cancer is ovarian cancer.

Embodiment 30. The method of Embodiment 27, wherein the cancer is gastric cancer.

Embodiment 31. The method of Embodiment 27, wherein the cancer is neuronal cancer.

Embodiment 32. The method of Embodiment 27, wherein the cancer is breast cancer.

Embodiment 33. The method of any one of Embodiments 24-27 and 32, wherein the compound inhibits mammosphere formation.

Embodiment 34. The method of any one of Embodiments 24-33, wherein the compound induces cell cycle arrest of a diseased cell.

Embodiment 35. The method of any one of Embodiments 24-34, wherein the compound induces apoptosis of a diseased cell.

Embodiment 36. The method of any one of Embodiments 24-35, wherein the compound reduces the expression of a Bcl-2 protein.

Embodiment 37. The method of any one of Embodiments 24-36, wherein the disease is mediated by a GTPase.

Embodiment 38. The method of Embodiment 37, wherein the GTPase is Rac 1 or Cdc42.

Embodiment 39. The method of Embodiment 38, wherein the GTPase is Rac1.

Embodiment 40. The method of Embodiment 38, wherein the GTPase is Cdc42.

Embodiment 41. The method of any one of Embodiments 24-40, wherein the compound inhibits PAK1/2 activity.

Embodiment 42. The method of any one of Embodiments 24-40, wherein the compound inhibits STAT3 activity.

Embodiment 43. The method of any one of Embodiments 24-42, wherein the effective amount of the compound is in a range of about 0.1 mg/kg to about 50 mg/kg of body weight of the patient.

Embodiment 44. The method of any one of Embodiments 24-42, wherein the effective amount of the compound is in a range of about 0.01 mg/kg to about 100 mg/kg of body weight of the patient.

Also provided are embodiments wherein any embodiment above may be combined with any one or more of these embodiments, provided the combination is not mutually exclusive.

As used herein, two embodiments are "mutually exclusive" when one is defined to be something which is different than the other. For example, an embodiment wherein two groups combine to form a cycloalkyl is mutually exclusive with an embodiment in which one group is ethyl the other group is hydrogen. Similarly, an embodiment wherein one group is $CH_2$ is mutually exclusive with an embodiment wherein the same group is NH.

Also provided is a compound chosen from the Examples disclosed herein.

The present disclosure also relates to a method of inhibiting at least one RhoGTPase function comprising the step of contacting RhoGTPase with a compound as described herein. The cell phenotype, cell proliferation, activity of RhoGTPase, change in biochemical output produced by active RhoGTPase, expression of RhoGTPase, or binding of RhoGTPase with a natural binding partner may be monitored. Such methods may be modes of treatment of disease, biological assays, cellular assays, biochemical assays, or the like.

Also provided herein is a method of treatment of a RhoGTPase-mediated disease comprising the administration of a therapeutically effective amount of a compound as disclosed herein, or a salt thereof, to a patient in need thereof.

In certain embodiments, the disease is a neurodegenerative disease.

Also provided herein is a compound as disclosed herein for use as a medicament.

Also provided herein is a compound as disclosed herein for use as a medicament for the treatment of a RhoGTPase-mediated disease.

Also provided is the use of a compound as disclosed herein as a medicament.

Also provided is the use of a compound as disclosed herein as a medicament for the treatment of a RhoGTPase-mediated disease.

Also provided is a compound as disclosed herein for use in the manufacture of a medicament for the treatment of a RhoGTPase-mediated disease.

Also provided is the use of a compound as disclosed herein for the treatment of a RhoGTPase-mediated disease.

Also provided herein is a method of inhibition of RhoGTPase comprising contacting RhoGTPase with a compound as disclosed herein, or a salt thereof.

Also provided is a method of modulation of a RhoGTPase-mediated function in a subject comprising the administration of a therapeutically effective amount of a compound as disclosed herein.

Also provided is a pharmaceutical composition comprising a compound as disclosed herein, together with a pharmaceutically acceptable carrier.

In certain embodiments, the pharmaceutical composition is formulated for oral administration.

In certain embodiments, the pharmaceutical composition is formulated for parenteral administration.

In certain embodiments, the oral pharmaceutical composition is chosen from a tablet and a capsule.

Abbreviations and Definitions

As used herein, the terms below have the meanings indicated.

When ranges of values are disclosed, and the notation "from $n_1$ ... to $n_2$" or "between $n_1$ ... and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 μM (micromolar)," which is intended to include 1 μM, 3 μM, and everything in between to any number of significant figures (e.g., 1.255 μM, 2.1 μM, 2.9999 μM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

As used herein, the term "essentially the same" with reference to X-ray diffraction peak positions means that typical peak position and intensity variability are taken into account. For example, one skilled in the art will appreciate that the peak positions (2θ) will show some variability, typically as much as 0.1 to 0.2 degrees, depending on the solvents being used, as well as on the apparatus being used to measure the diffraction. Further, one skilled in the art will appreciate that relative peak intensities will show inter-apparatus variability as well as variability due to degree of crystallinity, preferred orientation, prepared sample surface, and other factors known to those skilled in the art, and should be taken as qualitative measures only.

Similarly, as used herein, "essentially the same" with reference to solid state NMR spectra and Raman spectra is intended to also encompass the variabilities associated with these analytical techniques, which are known to those of skill in the art. For example, $^{13}C$ chemical shifts measured in solid state NMR will typically have a variability of up to 0.2 ppm for well-defined peaks, and even larger for broad lines, while Raman shifts will typically have a variability of about 2 cm 1.

The term "amorphous" refers to any solid substance which (i) lacks order in three dimensions, or (ii) exhibits order in less than three dimensions, order only over short distances (e.g., less than 10 A), or both. Thus, amorphous substances include partially crystalline materials and crystalline mesophases with, e.g. one- or two-dimensional translational order (liquid crystals), orientational disorder (orientationally disordered crystals), or conformational disorder (conformationally disordered crystals). Amorphous solids may be characterized by known techniques, including X-ray powder diffraction (XRPD) crystallography, solid state nuclear magnet resonance (ssNMR) spectroscopy, differential scanning calorimetry (DSC), or some combination of these techniques. As illustrated, below, amorphous solids give diffuse XRPD patterns, typically comprised of one or two broad peaks (i.e., peaks having base widths of about 5° 2 θ or greater).

The term "polymorph" refers to different crystalline forms of the same compound and includes, but is not limited to, other solid state molecular crystalline forms including hydrates (e.g., bound water present in the crystalline structure) and solvates (e.g., bound solvents other than water) of the same compound.

The term "crystalline" refers to any solid substance exhibiting three-dimensional order, which in contrast to an amorphous solid substance, gives a distinctive XRPD pattern with sharply defined peaks.

The term "solvate" describes a molecular complex comprising the drug substance and a stoichiometric or non-stoichiometric amount of one or more solvent molecules (e.g., ethanol). When the solvent is tightly bound to the drug the resulting complex will have a well-defined stoichiometry that is independent of humidity. When, however, the solvent is weakly bound, as in channel solvates and hygroscopic compounds, the solvent content will be dependent on humidity and drying conditions. In such cases, the complex will often be non-stoichiometric.

The term "hydrate" describes a solvate comprising the drug substance and a stoichiometric or non-stoichiometric amount of water.

The term "channel hydrate" refers to hydrate structures with open structural voids where the water molecules may fully or partly escape through the channels (voids) without significant changes in the crystal structure.

The term "2 theta value" or "2 θ" refers to the peak position in degrees based on the experimental setup of the X-ray diffraction experiment and is a common abscissa unit in diffraction patterns. The experimental setup requires that if a reflection is diffracted when the incoming beam forms an angle theta (θ) with a certain lattice plane, the reflected beam is recorded at an angle 2 theta (2 θ). It should be understood that reference herein to specific 2 θ values for a specific polymorphic form is intended to mean the 2 θ values (in degrees) as measured using the X-ray diffraction experimental conditions as described herein. For example, as described herein, CuKa (wavelength 1.54056 A) was used as the source of radiation The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O) $CH_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, said alkyl will comprise from 1 to 10 carbon atoms. In further embodiments, said alkyl will comprise from 1 to 8 carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, nonyl and the like. The term "alkylene," as used herein, alone or in combination, refers to a saturated aliphatic group derived from a straight or branched chain saturated hydrocarbon attached at two or more positions, such as methylene (—$CH_2$—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(O)N(RR') group with R and R' as defined herein or as defined by the specifically enumerated "R" groups designated. The term "N-amido" as used herein, alone or in combination, refers to a RC(O)N(R')— group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino ($CH_3$C(O) NH—).

The term "amino," as used herein, alone or in combination, refers to —NRR', wherein R and R' are independently chosen from hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term aryloxy as used herein, alone or in combination, refers to an aryl group attached to the parent molecular moiety through an oxy.

The term "carbonyl." as used herein, when alone includes formyl [—C(O)H] and in combination is a —C(O)— group.

The term "carboxyl" or "carboxy." as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl." or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 5 to 7 carbon atoms. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester." as used herein, alone or in combination, refers to a carboxy group bridging two moieties linked at carbon atoms.

The term "halo," or "halogen," as used herein, alone or in combination, refers to fluorine, chlorine, bromine, or iodine.

The term "heteroaryl," as used herein, alone or in combination, refers to a 3 to 15 membered unsaturated heteromonocyclic ring, or a fused monocyclic, bicyclic, or tricyclic ring system in which at least one of the fused rings is aromatic, which contains at least one atom chosen from N, O, and S. In certain embodiments, said heteroaryl will comprise from 1 to 4 heteroatoms as ring members. In further embodiments, said heteroaryl will comprise from 1 to 2 heteroatoms as ring members. In certain embodiments, said heteroaryl will comprise from 5 to 7 atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The term "hydroxy," as used herein, alone or in combination, refers to —OH.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, lower carbamate, and lower urea. Where structurally feasible, two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety chosen from hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R″ where n=(1, 2, 3 . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. For example, an unsymmetrical group such as —C(O)N(R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the disclosure encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present disclosure includes all cis, trans, syn, anti, entgegen (E), and zusammen (Z) isomers as well as the appropriate mixtures thereof. Additionally, compounds may exist as tautomers; all tautomeric isomers are provided by this disclosure. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

"RhoGTPase inhibitor" is used herein to refer to a compound that exhibits a $K_i$ with respect to RhoGTPase of no more than about 100 μM and more typically not more than about 50 μM, as measured in the RhoGTPase inhibition assay described generally herein.

The phrase "therapeutically effective" is intended to qualify the amount of active ingredients used in the treatment of a disease or disorder or on the effecting of a clinical endpoint.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

The term "prodrug" refers to a compound that is made more active in vivo. Certain compounds disclosed herein may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

The compounds disclosed herein can exist as therapeutically acceptable salts. The present disclosure includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to *Pharmaceutical Salts: Properties, Selection, and Use* (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, hydrogen citrate, dihydrogen citrate, digluconate, formate, fumarate, hydrogen fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, hydrogen maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, hydrogen succinate, sulfonate, tartrate, hydrogen tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present disclosure contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

Without intending to be limiting, salts comprising the following anions are contemplated in this disclosure:

Pharmaceutical Compositions

While it may be possible for the compounds of the subject disclosure to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject disclosure or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Administration and Treatment

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

Oral Administration

The compounds of the present disclosure may be administered orally, including swallowing, so the compound enters the gastrointestinal tract, or is absorbed into the blood stream directly from the mouth, including sublingual or buccal administration.

Suitable compositions for oral administration include solid formulations such as tablets, pills, cachets, lozenges and hard or soft capsules, which can contain liquids, gels, powders, or granules, solutions or suspensions in an aqueous liquid or a non-aqueous liquid, or as an oil-in-water liquid emulsion or a water-in-oil liquid emulsion. The active ingredient may also be presented as a bolus, electuary or paste.

In a tablet or capsule dosage form the amount of drug present may be from about 0.05% to about 95% by weight, more typically from about 2% to about 50% by weight of the dosage form.

In addition, tablets or capsules may contain a disintegrant, comprising from about 0.5% to about 35% by weight, more typically from about 2% to about 25% of the dosage form. Examples of disintegrants include methyl cellulose, sodium or calcium carboxymethyl cellulose, croscarmellose sodium, polyvinylpyrrolidone, hydroxypropyl cellulose, starch and the like.

Suitable binders, for use in a tablet, include gelatin, polyethylene glycol, sugars, gums, starch, hydroxypropyl cellulose and the like. Suitable diluents, for use in a tablet, include mannitol, xylitol, lactose, dextrose, sucrose, sorbitol and starch.

Suitable surface active agents and glidants, for use in a tablet or capsule, may be present in amounts from about 0.1% to about 3% by weight, and include polysorbate 80, sodium dodecyl sulfate, talc and silicon dioxide.

Suitable lubricants, for use in a tablet or capsule, may be present in amounts from about 0.1% to about 5% by weight, and include calcium, zinc or magnesium stearate, sodium stearyl fumarate and the like.

Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with a liquid diluent. Dyes or pigments may be added to tablets for identification or to characterize different combinations of active compound doses.

Liquid formulations can include emulsions, solutions, syrups, elixirs and suspensions, which can be used in soft or hard capsules. Such formulations may include a pharmaceutically acceptable carrier, for example, water, ethanol, polyethylene glycol, cellulose, or an oil. The formulation may also include one or more emulsifying agents and/or suspending agents.

Compositions for oral administration may be formulated as immediate or modified release, including delayed or sustained release, optionally with enteric coating.

In another embodiment, a pharmaceutical composition comprises a therapeutically effective amount of a compound of Formula (I) or a pharmaceutically acceptable salt thereof, and a pharmaceutically acceptable carrier.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Parenteral Administration

Compounds of the present disclosure may be administered directly into the blood stream, muscle, or internal organs by injection, e.g., by bolus injection or continuous infusion. Suitable means for parenteral administration include intravenous, intra-muscular, subcutaneous intraarterial, intraperitoneal, intrathecal, intracranial, and the like. Suitable devices for parenteral administration include injectors (including needle and needle-free injectors) and infusion methods. The formulations may be presented in unit-dose or multi-dose containers, for example scaled ampoules and vials.

Most parenteral formulations are aqueous solutions containing excipients, including salts, buffering, suspending, stabilizing and/or dispersing agents, antioxidants, bacteriostats, preservatives, and solutes which render the formulation isotonic with the blood of the intended recipient, and carbohydrates.

Parenteral formulations may also be prepared in a dehydrated form (e.g., by lyophilization) or as sterile non-aqueous solutions. These formulations can be used with a suitable vehicle, such as sterile water. Solubility-enhancing agents may also be used in preparation of parenteral solutions. Compositions for parenteral administration may be formulated as immediate or modified release, including delayed or sustained release. Compounds may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example scaled ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Topical Administration

Compounds of the present disclosure may be administered topically (for example to the skin, mucous membranes, ear, nose, or eye) or transdermally. Formulations for topical administration can include, but are not limited to, lotions, solutions, creams, gels, hydrogels, ointments, foams, implants, patches and the like. Carriers that are pharmaceutically acceptable for topical administration formulations can include water, alcohol, mineral oil, glycerin, polyethylene glycol and the like. Topical administration can also be performed by, for example, electroporation, iontophoresis, phonophoresis and the like.

Typically, the active ingredient for topical administration may comprise from 0.001% to 10% w/w (by weight) of the formulation. In certain embodiments, the active ingredient may comprise as much as 10% w/w; less than 5% w/w; from 2% w/w to 5% w/w; or from 0.1% to 1% w/w of the formulation.

Compositions for topical administration may be formulated as immediate or modified release, including delayed or sustained release.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

Rectal, Buccal, and Sublingual Administration

Suppositories for rectal administration of the compounds of the present disclosure can be prepared by mixing the active agent with a suitable non-irritating excipient such as cocoa butter, synthetic mono-, di-, or triglycerides, fatty acids, or polyethylene glycols which are solid at ordinary temperatures but liquid at the rectal temperature, and which will therefore melt in the rectum and release the drug.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Administration by Inhalation

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the disclosure may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Other carrier materials and modes of administration known in the pharmaceutical art may also be used. Pharmaceutical compositions of the disclosure may be prepared by any of the well-known techniques of pharmacy, such as effective formulation and administration procedures. Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Combinations and Combination Therapy

In certain instances, it may be appropriate to administer at least one of the compounds described herein (or a pharmaceutically acceptable salt thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

Specific, non-limiting examples of possible combination therapies include use of certain compounds of the disclosure with: donepezil, rivastigmine, galantamine, and memantine. Further examples include anti-amyloid antibodies and vaccines, anti-Ab antibodies and vaccines, anti-tau antibodies and vaccines, β-secretase inhibitors, 5-HT4 agonists, 5-HT6 antagonists, 5-HT1a antagonists, α7 nicotinic receptor agonists, 5-HT3 receptor antagonists, PDE4 inhibitors, O-GlcNAcase inhibitors, and other medicines approved for the treatment of Alzheimer's disease. Further examples include metformin, minocycline, tissue plasminogen activator, and other therapies that improve neuronal survival.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, certain embodiments provide methods for treating RhoGTPase-mediated disorders in a human or animal subject in need of such treatment comprising administering to said subject an amount of a compound disclosed herein effective to reduce or prevent said disorder in the subject, in combination with at least one additional agent for the treatment of said disorder that is known in the art. In a related aspect, certain embodiments provide therapeutic compositions comprising at least one compound disclosed herein, in combination with one or more additional agents for the treatment of RhoGTPase-mediated disorders.

In certain embodiments, the compounds, compositions, and methods disclosed herein may be useful for the treatment of hyperproliferative and neoplastic diseases. In certain further embodiments, the disease is cancer. In certain further embodiments, the cancer is chosen from breast cancer, prostate cancer, neuroblastoma, ovarian cancer, pancreatic cancer, and gastric cancer.

In certain embodiments, the compounds, compositions, and methods disclosed herein may be coadministered with another therapeutic agent.

In certain embodiments, the compounds, compositions, and methods disclosed herein may be coadministered with another therapeutic agent for the treatment of cancer.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

Compound Synthesis

Compounds of the present disclosure can be prepared using methods illustrated in general synthetic schemes and experimental procedures detailed below. General synthetic schemes and experimental procedures are presented for purposes of illustration and are not intended to be limiting. Starting materials used to prepare compounds of the present disclosure are commercially available or can be prepared using routine methods known in the art.

List of Abbreviations $Ac_2O$=acetic anhydride; AcCl=acetyl chloride; AcOH=acetic acid; $CD_3OD$=deuterated methanol; $CDCl_3$=deuterated chloroform; DCM=dichloromethane; DIEA=DIPEA=N,N-diisopropylethylamine; DMAP=4-dimethylaminopyridine; DMF=N,N-dimethylformamide; DMSO-$d_6$=deuterated dimethyl sulfoxide; DMSO=dimethyl sulfoxide; DPPA=$Et_2O$=diethyl ether; DSC=differential scanning calorimetry; EtOAc=ethyl acetate; EtOH=ethanol; h=hour; FaSSIF=fasted state simulated intestinal fluid; FeSSIF=fed state simulated intestinal fluid; FTIR=Fourier transform infrared spectroscopy; i-PrOH=isopropanol; MeCN=acetonitrile; MeOH=methanol; MTBE=methyl tertiary butyl ether; NMP=N-Methyl-2-pyrrolidone; PXRD=XRPD=powder X-ray diffraction; Pyr=pyridine; RT=room temperature; sat.=saturated; ss=saturated solution; SCXRD=single crystal X-ray diffraction; SGF=simulated gastric fluid; t-BuOH=tert-butanol; TEA=$Et_3N$=triethylamine; Teoc=(2-trimethylsilylethoxy)carbonyl; TGA=thermogravimetric analysis; THF=tetrahydrofuran; Tol=toluene.

Methods

Differential Scanning calorimetry (DSC) DSC was performed to determine the melting temperature ($T_m$) and enthalpy of fusion ($\Delta_{fus}H$) of MBQ-167. A differential scanning calorimeter (DSC) from TA Instruments Inc. (Q2000) equipped with a RCS40 single-stage refrigeration system was employed to carry out these measurements. The calibration of the DSC was conducted with an indium standard ($T_m$=156.6° C. and $\Delta_{fus}H$=28.54 J/g). Between 1.000-3.000 mg of the crystalline sample was weighed using a XP26 microbalance from Mettler Toledo (±0.002 mg) and placed on Tzero aluminum pans that were hermetically sealed. Samples were equilibrated at 25° C. for 5 min before heating to 250° C. at a rate of 5.0° C./min and then was cooled to 25° C. at a heating rate of 10° C./min under a $N_2$ atmosphere (50 mL/min) and a temperature accuracy of 0.1° C.

Thermogravimetric Analysis (TGA) Thermographs were recorded in a Thermogravimetric Analyzer (TGA) from TA Instruments Inc. (Q500) calibrated with calcium oxalate monohydrate ($CaC_2O_4 \cdot H_2O$) standard to determine if MBQ-167 degrades before melting. Between 1.000-2.000 mg of the crystalline sample were equilibrated at 25° C. for 5 min before heating to 400° C. under $N_2$ atmosphere (60 mL/min) at a rate of 5.0° C./min and a temperature accuracy of 0.1° C. Data was analyzed with the TA Universal Analysis 2000 software (version 4.5A). TGA reveals that MBQ-167 starts to decompose after the melting temperature.

Single Crystal X-ray Diffraction (SCXRD) The crystals were observed under the microscope using polarized light to assess their quality. Optical micrographs were recorded with a Nikon Eclipse Microscope LV100NPOL, equipped with a Nikon DS-Fi2 camera and NIS Elements BR software version 4.30.01. Suitable single crystals were mounted in MiTeGen micro loops for structure elucidation. Crystal structures were collected with a Rigaku XtaLAB SuperNova single micro-focus Cu-Kα radiation (λ=1.5417 Å) source equipped with a HyPix3000 X-ray detector in transmission mode operating at 50 kV and 1 mA within the CrystAllis$^{PRO}$ software (v. 1.171.39.46). The data collection was carried out at 100 K and 300 K using an Oxford Cryosystems Cryostream 800 cooler. All crystal structures were solved by direct methods. The refinement was performed using full-matrix least squares on F2 within the Olex2 software v1.2. All non-hydrogen atoms were anisotropically refined.

Powder X-ray Diffraction (PXRD) Powder diffractograms were collected at 100 and 300 K using a Rigaku XtaLAB SuperNova single micro-focus Cu-Kα radiation (λ=1.5417 Å) source equipped with a HyPix3000 X-ray detector operating at 50 kV and 1 mA in transmission mode. Solid samples were placed in MiTeGen micro loops with a slight amount of paratone oil. Diffractograms were collected over an angular 2θ range between 6-60° (step size of) 0.01° using the Gandolfi move experiment for powders with an exposure time of 120 s and a distance of 100 mm. Data was analyzed within the CrystAllis$^{PRO}$ software (v. 1.171.39.46).

Fourier Transform Infrared Spectroscopy (FTIR) FTIR spectra were collected using a Bruker Tensor-27 attenuated total reflectance spectrometer between 400 and 4000 cm$^{-1}$ with a resolution of 4 cm$^{-1}$ averaging 32 scans (1 scan/s). The data were collected with the OPUS Data Collection Program version 7.2.

Example 1: 9-Ethyl-3-(5-phenyl-1H-1,2,3-triazol-1-yl)-9H-carbazole ("MBQ-167") Form I

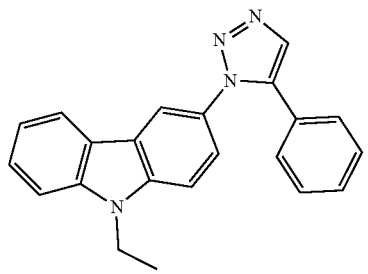 [SMILES: CCn1c2ccccc2c2cc(-n3nncc3-c3ccccc3)ccc21]

The Form I polymorph of MBQ-167 was obtained by MBQ-167 was obtained by recrystallization from ethanol of the material.

Example 2: 9-Ethyl-3-(5-phenyl-1H-1,2,3-triazol-1-yl)-9H-carbazole ("MBQ-167") Form II

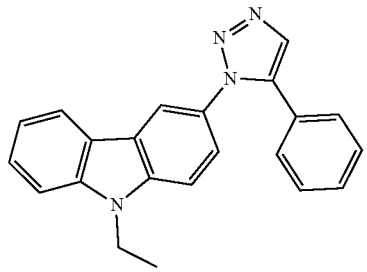 [SMILES: CCn1c2ccccc2c2cc(-n3nncc3-c3ccccc3)ccc21]

The Form II polymorph of MBQ-167 was obtained by recrystallization from 33% (volume/volume) ethyl acetate/heptane of the material.

Example 3: Calorimetric Analysis

A DSC thermograph of the Form I polymorph is shown in FIG. 1. An endothermic peak, with an onset of 152.46° C. and centered at 153.48° C., corresponding to 0.4908 W/g is observed for the Form I polymorph.

Figure 2:
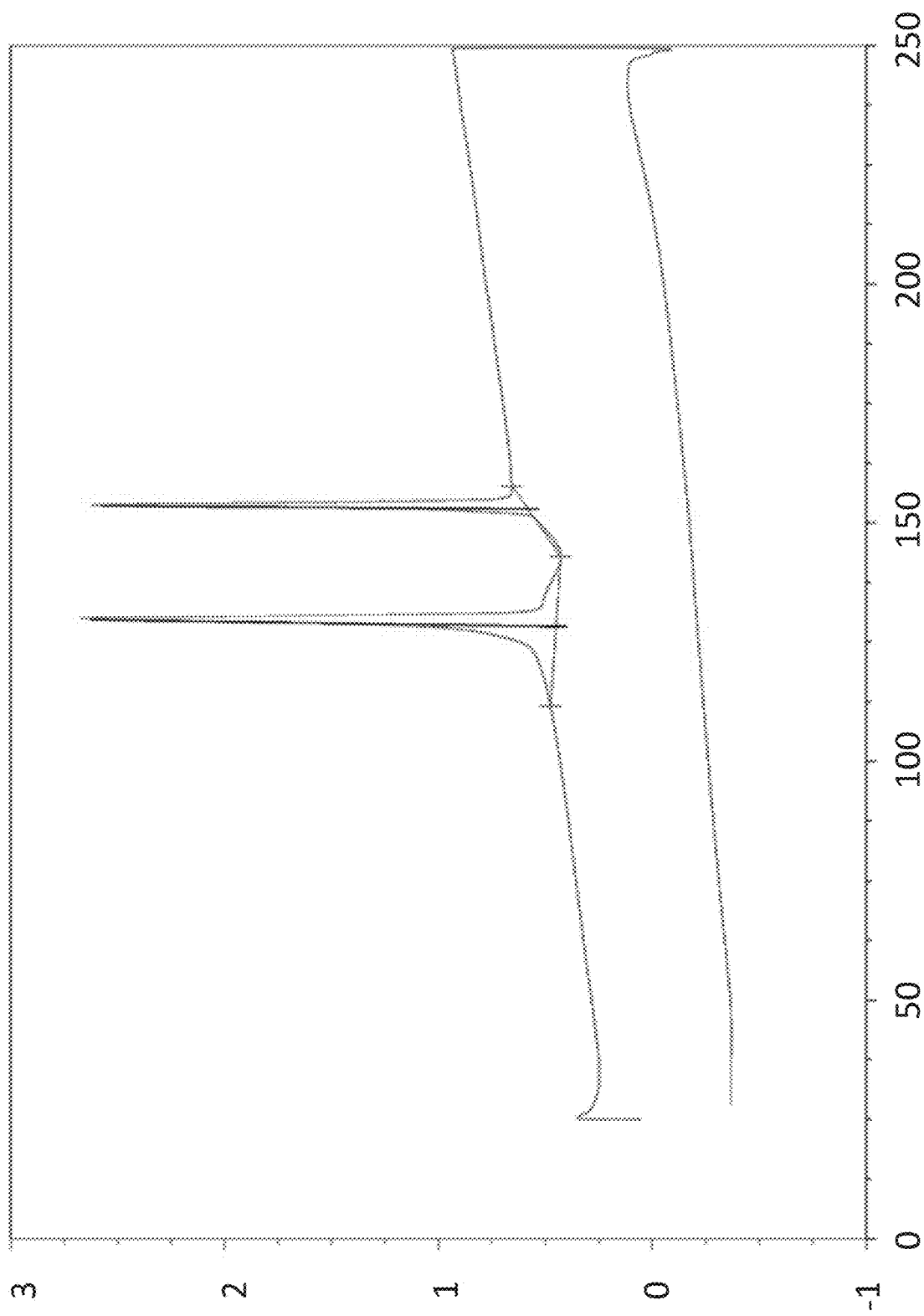
FIG. 2 shows a DSC thermograph of the Form II polymorph. Horizontal axis=temp (C); vertical axis=heat flow (mW).

A DSC thermograph of the Form II polymorph is shown in FIG. 2. A first endothermic peak, with an onset of 128.22° C. and centered at 129.82° C., corresponding to 0.4504 W/g, is followed by a second endothermic peak, with an onset of 152.81° C. and centered at 153.64° C., corresponding to 0.5809 W/g.

Figure 3:
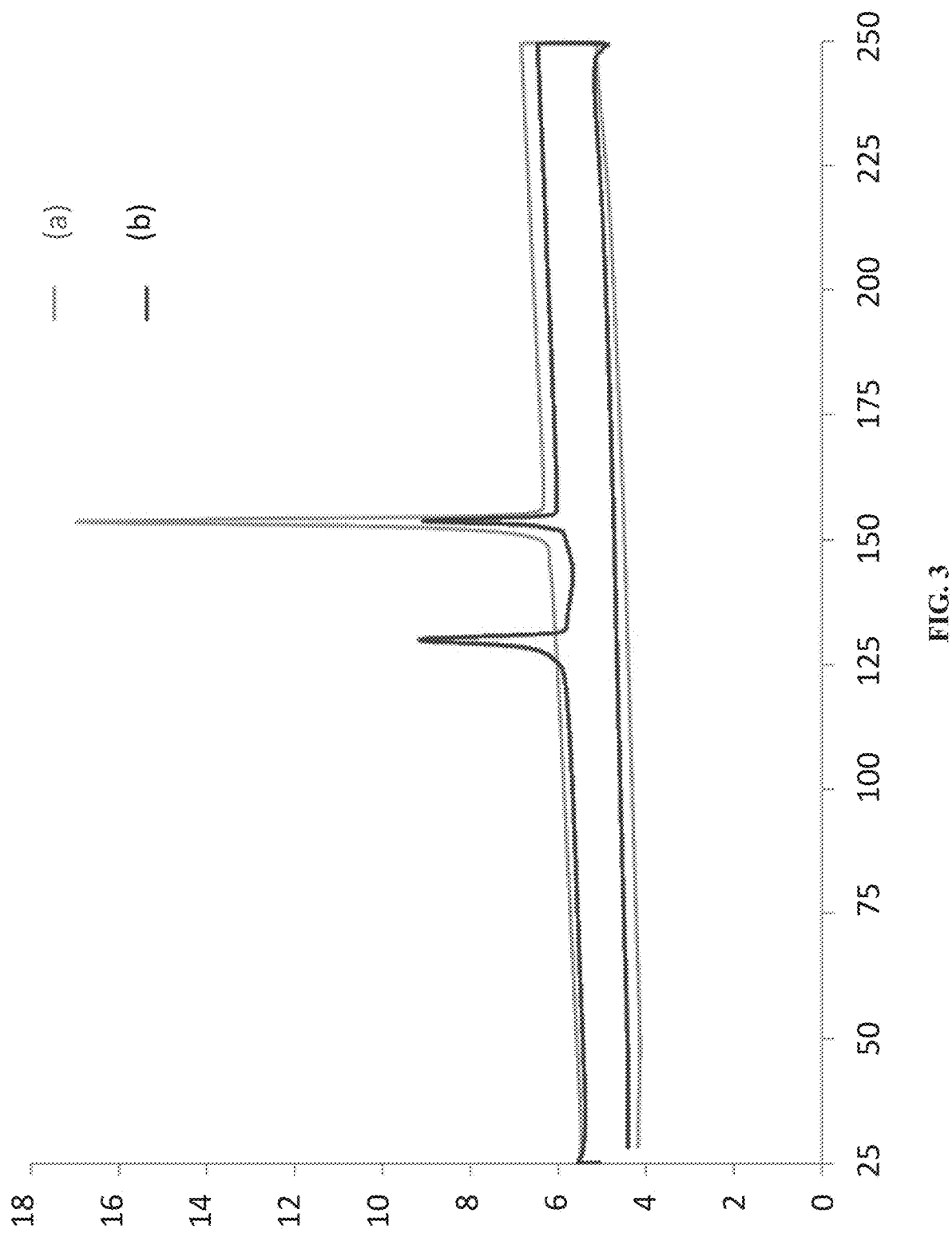
FIG. 3 shows an overlay for the DSC thermographs of (a) the Form I polymorph and (b) Form II polymorph. Horizontal axis=temp (° C.); vertical axis=heat flow (mW).

Overlay of the two DSC thermographs, shown in FIG. 3, makes apparent the source of the behavior of the Form II polymorph. The Form I polymorph undergoes a single endothermic phase transition to the melt. The lower temperature endotherm for the Form II polymorph represents a phase transition to the more stable Form I polymorph. Upon prolonged heating, this material then undergoes phase transition to the melt, the endotherm for which occurs at the same temperature as authentic Form I polymorph, confirming this hypothesis.

Example 4: Thermogravimetric Analysis

Figure 4:
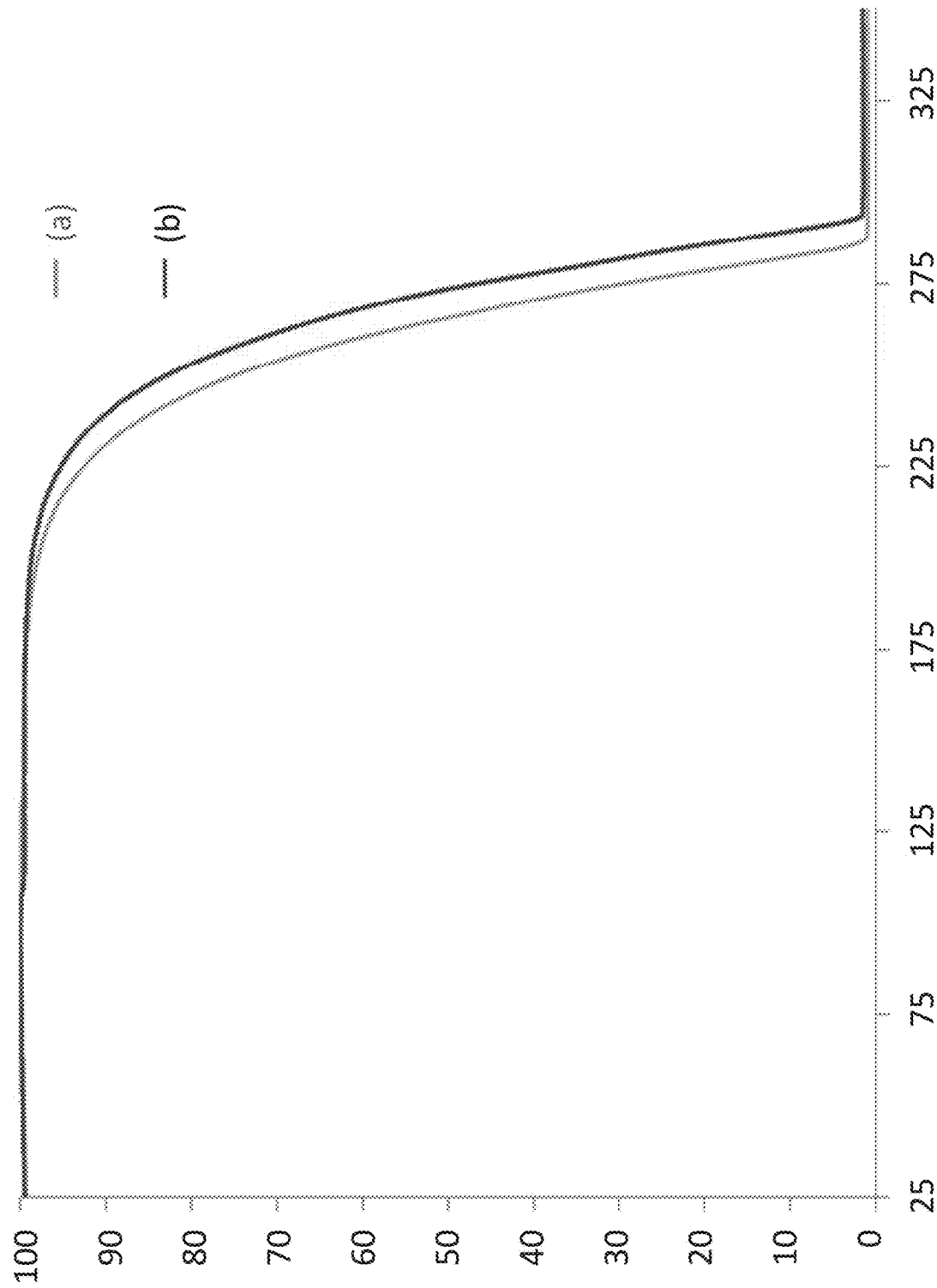
FIG. 4 shows an overlay for the TGA thermographs of (a) the Form I polymorph and (b) Form II polymorph. Horizontal axis=temp (° C.); vertical axis=weight (%).

The two polymorphs were subjected to thermogravimetric analysis, with results shown in FIG. 4. Decomposition of the Form I polymorph (a) begins at about 184.7° C., while onset for decomposition of the Form II polymorph (b) begins at about 193.0° C.

Example 5: SCXRD of the Form I Polymorph

SCXRD analysis was performed on the Form I polymorph from Example 1 at both 100 K and 300 K.

Figure 5:
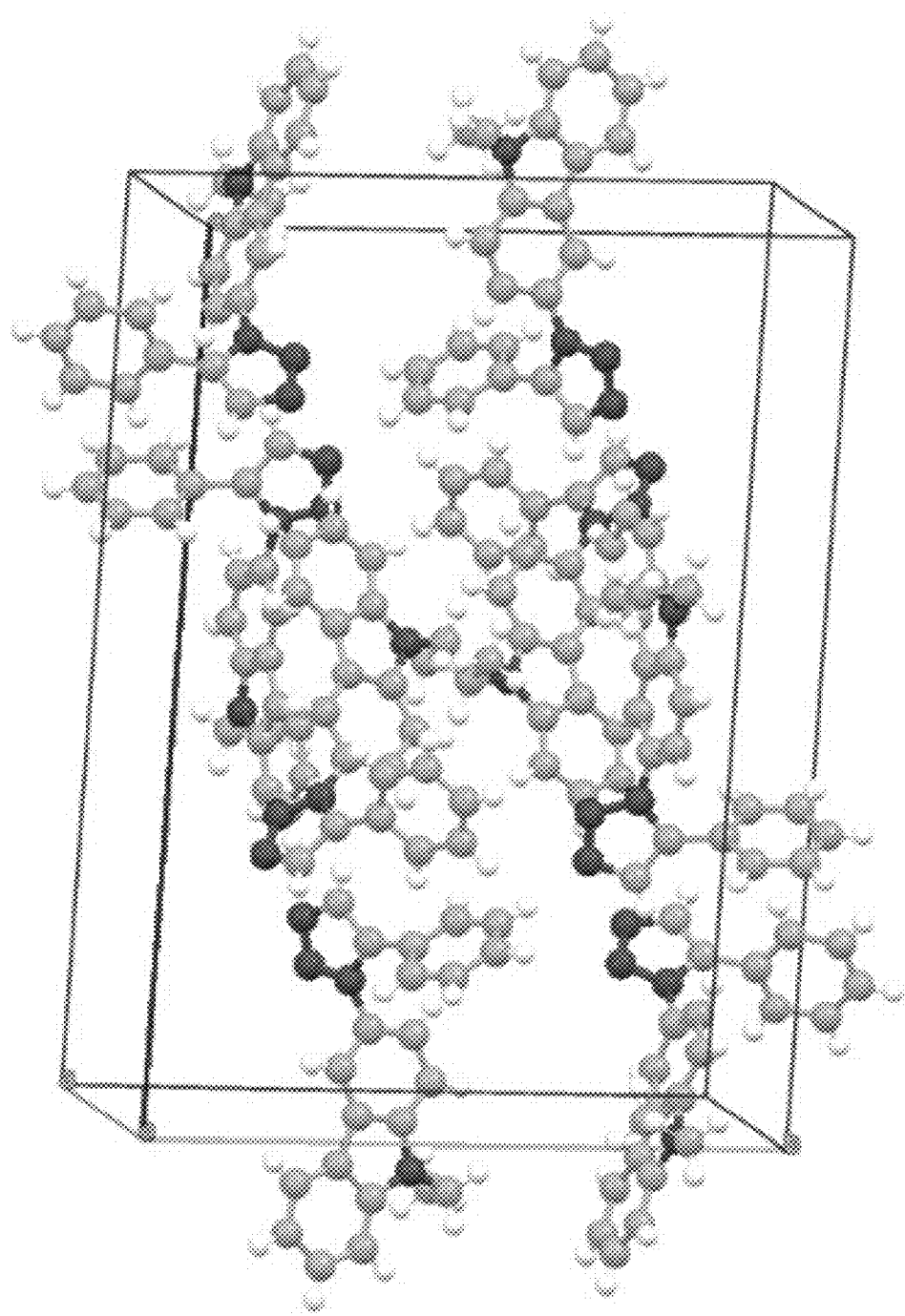
FIG. 5 shows the unit cell contents for the Form I polymorph at 100 K.

100 K Data collection and refinement: Orthorhombic, Pbca; a=7.57408(5) Å; b=17.87230(12) Å; c=24.98583(16) Å; V=3382.23(4) Å$^3$; Z=8; multi-scan absorption correction; $T_{max}/T_{min}$=1.0000/0.34182; 20767 total reflections; 3115 observed reflections; 2961 reflections with I>2σ(I)°; $R_1$ (I>2σ(I))=0.0405; $wR_2$ (all)=0.1027; Δρ max/min=0.18/−0.34 e/Å$^3$. FIG. 5 shows the unit cell contents as obtained from this study.

TABLE 1

Atomic coordinates for the Form I polymorph at 100K.

| Label | Type | x | y | z | U | (a) | (b) | (c) |
|---|---|---|---|---|---|---|---|---|
| N1 | N | 0.75944(15) | 0.26910(6) | 0.26640(4) | 0.0190(3) | Uani | d | — |
| N2 | N | 0.68922(15) | 0.27346(6) | 0.31419(4) | 0.0174(2) | Uani | d | — |
| N3 | N | 0.72813(14) | 0.34286(6) | 0.33368(4) | 0.0147(2) | Uani | d | — |
| N4 | N | 0.40381(13) | 0.40586(6) | 0.52719(4) | 0.0146(2) | Uani | d | — |
| C1 | C | 0.84050(17) | 0.33510(7) | 0.25505(5) | 0.0180(3) | Uani | d | — |
| H1 | H | 0.899112 | 0.346047 | 0.223295 | 0.022 | Uiso | calc | R |
| C2 | C | 0.82276(16) | 0.38292(7) | 0.29741(5) | 0.0147(3) | Uani | d | — |
| C3 | C | 0.88729(16) | 0.46005(7) | 0.30608(5) | 0.0146(3) | Uani | d | — |
| C4 | C | 0.82137(18) | 0.51762(7) | 0.27429(5) | 0.0198(3) | Uani | d | — |
| H4 | H | 0.735100 | 0.507403 | 0.248836 | 0.024 | Uiso | calc | R |
| C5 | C | 0.88371(18) | 0.59022(7) | 0.28039(6) | 0.0219(3) | Uani | d | — |
| H5 | H | 0.838463 | 0.628495 | 0.259227 | 0.026 | Uiso | calc | R |
| C6 | C | 1.01308(18) | 0.60565(7) | 0.31791(5) | 0.0199(3) | Uani | d | — |
| H6 | H | 1.054885 | 0.654247 | 0.321976 | 0.024 | Uiso | calc | R |
| C7 | C | 1.08028(18) | 0.54844(8) | 0.34947(5) | 0.0198(3) | Uani | d | — |
| H7 | H | 1.168103 | 0.558767 | 0.374408 | 0.024 | Uiso | calc | R |
| C8 | C | 1.01707(17) | 0.47569(7) | 0.34403(5) | 0.0179(3) | Uani | d | — |
| H8 | H | 1.061255 | 0.437672 | 0.365624 | 0.021 | Uiso | calc | R |
| C9 | C | 0.65234(16) | 0.36556(7) | 0.38380(5) | 0.0144(3) | Uani | d | — |
| C10 | C | 0.70402(16) | 0.32958(7) | 0.43007(5) | 0.0141(3) | Uani | d | — |
| H10 | H | 0.795285 | 0.294777 | 0.429757 | 0.017 | Uiso | calc | R |
| C11 | C | 0.61497(16) | 0.34707(7) | 0.47741(5) | 0.0134(3) | Uani | d | — |
| C12 | C | 0.62569(16) | 0.31987(7) | 0.53173(5) | 0.0137(3) | Uani | d | — |
| C13 | C | 0.73431(17) | 0.26773(7) | 0.55734(5) | 0.0172(3) | Uani | d | — |
| H13 | H | 0.822634 | 0.242921 | 0.538531 | 0.021 | Uiso | calc | R |
| C14 | C | 0.70776(18) | 0.25376(8) | 0.61129(5) | 0.0200(3) | Uani | d | — |
| H14 | H | 0.779052 | 0.219198 | 0.628817 | 0.024 | Uiso | calc | R |
| C15 | C | 0.57483(18) | 0.29105(8) | 0.63979(5) | 0.0203(3) | Uani | d | — |
| H15 | H | 0.560064 | 0.280837 | 0.676013 | 0.024 | Uiso | calc | R |
| C16 | C | 0.46500(17) | 0.34269(7) | 0.61539(5) | 0.0179(3) | Uani | d | — |
| H16 | H | 0.376391 | 0.366986 | 0.634413 | 0.021 | Uiso | calc | R |
| C17 | C | 0.49257(16) | 0.35692(7) | 0.56091(5) | 0.0144(3) | Uani | d | — |
| C18 | C | 0.23941(17) | 0.44464(7) | 0.53973(5) | 0.0183(3) | Uani | d | — |
| H18A | H | 0.237404 | 0.492408 | 0.521315 | 0.022 | Uiso | calc | R |
| H18B | H | 0.234425 | 0.454379 | 0.577894 | 0.022 | Uiso | calc | R |
| C19 | C | 0.07874(18) | 0.39926(9) | 0.52335(6) | 0.0257(3) | Uani | d | — |
| H19A | H | 0.083909 | 0.389034 | 0.485661 | 0.038 | Uiso | calc | GR |
| H19B | H | −0.026503 | 0.427101 | 0.531213 | 0.038 | Uiso | calc | GR |
| H19C | H | 0.077234 | 0.352950 | 0.542813 | 0.038 | Uiso | calc | GR |
| C20 | C | 0.47530(16) | 0.40008(7) | 0.47650(5) | 0.0139(3) | Uani | d | — |

TABLE 1-continued

Atomic coordinates for the Form I polymorph at 100K.

| Label | Type | x | y | z | U | (a) | (b) | (c) |
|---|---|---|---|---|---|---|---|---|
| C2 | C | 0.42774(17) | 0.43721(7) | 0.42967(5) | 0.0163(3) | Uani | d | — |
| H21 | H | 0.338100 | 0.472775 | 0.429674 | 0.020 | Uiso | calc | R |
| C22 | C | 0.51752(17) | 0.41971(7) | 0.38322(5) | 0.0161(3) | Uani | d | — |
| H22 | H | 0.488738 | 0.443831 | 0.351414 | 0.019 | Uiso | calc | R |

(a): thermal parameters:
Uiso = isotropic
Uani = anisotropic
(b): geometry:
d = from diffraction data
calc = calculated from molecular geometry
(c): constraints/restraints on xyz:
R = riding-atom site attached to non-riding atom
G = rigid-group refinement
(d) constraints/restraints on adp:
U = Uiso or Uij restraint (rigid bond)

300 K Data collection and refinement: Orthorhombic. Pbca; a=7.71100(10) Å; b=17.96460(10) Å; c=25.2167(2) Å; V=3493.14(6) Å$^3$; Z=8; 21532 total reflections; 3219 unique reflections; 2814 reflections with I>2σ(I) °; $R_1$ (I>2σ(I))=0.0562; $wR_2$ (all)=0.1531.

TABLE 2

Atomic coordinates for the Form I polymorph at 300K.

| Label | Type | x | y | z | U | (a) | (b) | (c) | (d) |
|---|---|---|---|---|---|---|---|---|---|
| N1 | N | 0.7603(2) | 0.25738(8) | 0.26989(6) | 0.0604(4) | Uani | d | — | — |
| N2 | N | 0.68956(19) | 0.26368(7) | 0.31670(6) | 0.0550(4) | Uani | d | — | — |
| N3 | N | 0.72765(16) | 0.33311(7) | 0.33462(5) | 0.0449(3) | Uani | d | — | — |
| N4 | N | 0.41037(16) | 0.40688(7) | 0.52442(5) | 0.0473(3) | Uani | d | — | — |
| C1 | C | 0.8417(2) | 0.32204(9) | 0.25775(7) | 0.0570(4) | Uani | d | — | — |
| H1 | H | 0.901639 | 0.331386 | 0.226456 | 0.068 | Uiso | calc | R | U |
| C2 | C | 0.82215(19) | 0.37132(8) | 0.29847(6) | 0.0451(4) | Uani | d | — | — |
| C3 | C | 0.88483(19) | 0.44824(8) | 0.30587(6) | 0.0442(4) | Uani | d | — | — |
| C4 | C | 0.8226(3) | 0.50421(9) | 0.27369(8) | 0.0640(5) | Uani | d | — | — |
| H4 | H | 0.740659 | 0.493334 | 0.247774 | 0.077 | Uiso | calc | R | U |
| C5 | C | 0.8815(3) | 0.57661(10) | 0.27971(9) | 0.0734(6) | Uani | d | — | — |
| H5 | H | 0.837483 | 0.614156 | 0.258185 | 0.088 | Uiso | calc | R | U |
| C6 | C | 1.0035(2) | 0.59309(9) | 0.31696(8) | 0.0639(5) | Uani | d | — | — |
| H6 | H | 1.043829 | 0.641621 | 0.320567 | 0.077 | Uiso | calc | R | U |
| C7 | C | 1.0663(2) | 0.53819(10) | 0.34894(7) | 0.0631(5) | Uani | d | — | — |
| H7 | H | 1.149650 | 0.549483 | 0.374341 | 0.076 | Uiso | calc | R | U |
| C8 | C | 1.0070(2) | 0.46558(9) | 0.34397(7) | 0.0563(4) | Uani | d | — | — |
| H8 | H | 1.049448 | 0.428617 | 0.366286 | 0.068 | Uiso | calc | R | U |
| C9 | C | 0.65136(19) | 0.35797(8) | 0.38360(6) | 0.0433(3) | Uani | d | — | — |
| C10 | C | 0.70379(18) | 0.32559(8) | 0.43045(6) | 0.0417(3) | Uani | d | — | — |
| H10 | H | 0.794263 | 0.291371 | 0.431145 | 0.050 | Uiso | calc | R | U |
| C11 | C | 0.61694(17) | 0.34573(7) | 0.47682(6) | 0.0394(3) | Uani | d | — | — |
| C12 | C | 0.62936(18) | 0.32262(7) | 0.53150(6) | 0.0415(3) | Uani | d | — | — |
| C13 | C | 0.7374(2) | 0.27340(9) | 0.55853(7) | 0.0518(4) | Uani | d | — | — |
| H13 | H | 0.824909 | 0.248031 | 0.540704 | 0.062 | Uiso | calc | R | U |
| C14 | C | 0.7125(3) | 0.26294(11) | 0.61203(7) | 0.0626(5) | Uani | d | — | — |
| H14 | H | 0.783428 | 0.229920 | 0.630385 | 0.075 | Uiso | calc | R | U |
| C15 | C | 0.5827(2) | 0.30109(10) | 0.63908(7) | 0.0632(5) | Uani | d | — | — |
| H15 | H | 0.569101 | 0.293276 | 0.675299 | 0.076 | Uiso | calc | R | U |
| C16 | C | 0.4737(2) | 0.35016(10) | 0.61348(7) | 0.0562(4) | Uani | d | — | — |
| H16 | H | 0.386681 | 0.375221 | 0.631727 | 0.067 | Uiso | calc | R | U |
| C17 | C | 0.49868(18) | 0.36088(8) | 0.55930(6) | 0.0444(4) | Uani | d | — | — |
| C18 | C | 0.24755(19) | 0.44524(10) | 0.53575(8) | 0.0575(4) | Uani | d | — | — |
| H18A | H | 0.242106 | 0.490610 | 0.514955 | 0.069 | Uiso | calc | R | U |
| H18B | H | 0.244893 | 0.459049 | 0.572929 | 0.069 | Uiso | calc | R | U |
| C19 | C | 0.0916(2) | 0.39793(12) | 0.52338(10) | 0.0810(6) | Uani | d | — | — |
| H19A | H | 0.093872 | 0.383945 | 0.486641 | 0.122 | Uiso | calc | R | U |
| H19B | H | −0.012143 | 0.425680 | 0.530571 | 0.122 | Uiso | calc | R | U |
| H19C | H | 0.093671 | 0.353984 | 0.545030 | 0.122 | Uiso | calc | R | U |
| C20 | C | 0.47909(18) | 0.39784(7) | 0.47409(6) | 0.0421(3) | Uani | d | — | — |
| C21 | C | 0.4318(2) | 0.43146(8) | 0.42677(6) | 0.0502(4) | Uani | d | — | — |
| H21 | H | 0.343554 | 0.466720 | 0.425662 | 0.060 | Uiso | calc | R | U |
| C22 | C | 0.5195(2) | 0.41104(8) | 0.38140(6) | 0.0496(4) | Uani | d | — | — |
| H22 | H | 0.490587 | 0.432789 | 0.349118 | 0.060 | Uiso | calc | R | U |

Example 6: SCXRD of the Form II Polymorph

SCXRD analysis was performed on the Form II polymorph from Example 2 at both 100 K and 300 K.

100 K Data collection and refinement: Monoclinic, P2$_1$/n; a=11.84900(10) Å; b=9.35910(10) Å; c=16.9689(2) Å; β=110.1710(10); V=1766.37(3) Å$^3$; Z=4; 17830 total reflections; 3267 unique reflections; 2992 reflections with I>2σ(I)°; R$_1$ (I>2σ(I))=0.0347; wR$_2$ (all)=0.0878.

TABLE 3

Atomic coordinates for the Form II polymorph at 100K.

| Label | Type | x | y | z | U | | | |
|---|---|---|---|---|---|---|---|---|
| N1 | N | 0.36044(8) | 0.38015(10) | 0.94918(6) | 0.0200(2) | Uani | d | — |
| N2 | N | 0.41835(8) | 0.34990(10) | 0.89782(6) | 0.0195(2) | Uani | d | — |
| N3 | N | 0.43453(8) | 0.47490(9) | 0.86223(6) | 0.0168(2) | Uani | d | — |
| N4 | N | 0.71495(8) | 0.43823(11) | 0.66089(6) | 0.0212(2) | Uani | d | — |
| C1 | C | 0.34071(10) | 0.52316(12) | 0.94704(7) | 0.0189(2) | Uani | d | — |
| H1 | H | 0.301865 | 0.571145 | 0.978366 | 0.023 | Uiso | calc | R |
| C2 | C | 0.38686(9) | 0.58641(12) | 0.89151(7) | 0.0168(2) | Uani | d | — |
| C3 | C | 0.38322(9) | 0.73545(12) | 0.86352(7) | 0.0175(2) | Uani | d | — |
| C4 | C | 0.38882(10) | 0.84490(13) | 0.92067(7) | 0.0214(2) | Uani | d | — |
| H4 | H | 0.399006 | 0.822686 | 0.976124 | 0.026 | Uiso | calc | R |
| C5 | C | 0.37926(10) | 0.98679(13) | 0.89516(8) | 0.0236(3) | Uani | d | — |
| H5 | H | 0.382349 | 1.059184 | 0.933389 | 0.028 | Uiso | calc | R |
| C6 | C | 0.36513(10) | 1.02058(12) | 0.81272(8) | 0.0224(3) | Uani | d | — |
| H6 | H | 0.359084 | 1.115594 | 0.795722 | 0.027 | Uiso | calc | R |
| C7 | C | 0.36000(10) | 0.91249(12) | 0.75562(7) | 0.0205(2) | Uani | d | — |
| H7 | H | 0.350554 | 0.935389 | 0.700372 | 0.025 | Uiso | calc | R |
| C8 | C | 0.36889(10) | 0.77041(12) | 0.78045(7) | 0.0188(2) | Uani | d | — |
| H8 | H | 0.365317 | 0.698439 | 0.741879 | 0.023 | Uiso | calc | R |
| C9 | C | 0.50665(10) | 0.47457(12) | 0.80953(7) | 0.0172(2) | Uani | d | — |
| C10 | C | 0.46825(10) | 0.39695(12) | 0.73575(7) | 0.0185(2) | Uani | d | — |
| H10 | H | 0.394399 | 0.350356 | 0.718178 | 0.022 | Uiso | calc | R |
| C11 | C | 0.54390(10) | 0.39078(12) | 0.68851(7) | 0.0187(2) | Uani | d | — |
| C12 | C | 0.53573(10) | 0.32098(12) | 0.61085(7) | 0.0216(2) | Uani | d | — |
| C13 | C | 0.44973(11) | 0.23403(15) | 0.55473(8) | 0.0312(3) | Uani | d | — |
| H13 | H | 0.379281 | 0.210528 | 0.564295 | 0.037 | Uiso | calc | R |
| C14 | C | 0.47078(13) | 0.18321(17) | 0.48459(9) | 0.0390(4) | Uani | d | — |
| H14 | H | 0.413994 | 0.125042 | 0.446645 | 0.047 | Uiso | calc | R |
| C15 | C | 0.57659(13) | 0.21842(16) | 0.47017(9) | 0.0363(3) | Uani | d | — |
| H15 | H | 0.588551 | 0.183368 | 0.422370 | 0.044 | Uiso | calc | R |
| C16 | C | 0.66385(11) | 0.30367(14) | 0.52477(8) | 0.0281(3) | Uani | d | — |
| H16 | H | 0.734062 | 0.326479 | 0.514696 | 0.034 | Uiso | calc | R |
| C17 | C | 0.64251(10) | 0.35433(13) | 0.59578(7) | 0.0218(3) | Uani | d | — |
| C18 | C | 0.83117(10) | 0.49814(14) | 0.66680(8) | 0.0248(3) | Uani | d | — |
| H18A | H | 0.871263 | 0.433098 | 0.640531 | 0.030 | Uiso | calc | R |
| H18B | H | 0.880795 | 0.507148 | 0.725487 | 0.030 | Uiso | calc | R |
| C19 | C | 0.81941(12) | 0.64301(14) | 0.62507(9) | 0.0313(3) | Uani | d | — |
| H19A | H | 0.768238 | 0.635289 | 0.567388 | 0.047 | Uiso | calc | GR |
| H19B | H | 0.897414 | 0.676001 | 0.627852 | 0.047 | Uiso | calc | GR |
| H19C | H | 0.785139 | 0.709636 | 0.653499 | 0.047 | Uiso | calc | GR |
| C20 | C | 0.65562(10) | 0.46323(12) | 0.71662(7) | 0.0192(2) | Uani | d | — |
| C21 | C | 0.69176(10) | 0.54444(12) | 0.79027(7) | 0.0209(2) | Uani | d | — |
| H21 | H | 0.764244 | 0.593969 | 0.807449 | 0.025 | Uiso | calc | R |
| C22 | C | 0.61621(10) | 0.54872(12) | 0.83672(7) | 0.0193(2) | Uani | d | — |
| H22 | H | 0.638173 | 0.601096 | 0.886303 | 0.023 | Uiso | calc | R |

Figure 6:
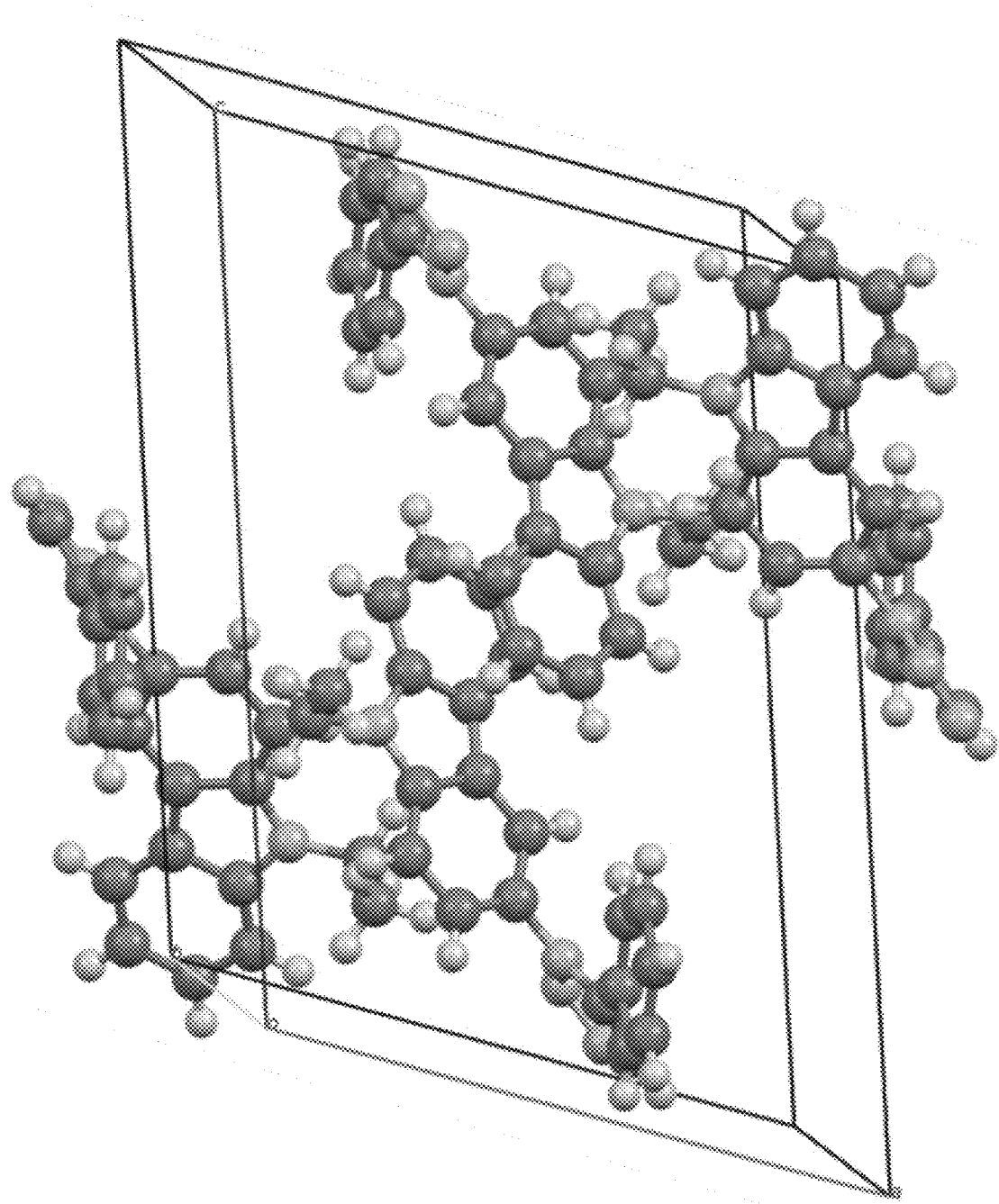
FIG. 6 shows the unit cell contents for the Form II polymorph at 300 K.

300 K Data collection and refinement: Monoclinic, P2$_1$/n; a=12.0906(2) Å; b=9.42800(10) Å; c=16.9628(2) Å; β=109.726(2)°; V=1820.12(5) Å$^3$; Z=4; 18746 total reflections; 3360 unique reflections; 2710 reflections with I>2σ(1)°; R$_1$ (I>2σ(I))=0.0531; wR$_2$ (all)=0.1645. FIG. 6 shows the unit cell contents as obtained from this study.

TABLE 4

Atomic coordinates for the Form II polymorph at 300K.

| Label | Type | x | y | z | U | (a) | (b) | (c) |
|---|---|---|---|---|---|---|---|---|
| N1 | N | 0.36078(15) | 0.38133(18) | 0.94671(11) | 0.0625(4) | Uani | d | — |
| H1 | H | 0.338998 | 0.320461 | 0.976294 | 0.075 | Uiso | calc | R |
| N2 | N | 0.41889(15) | 0.35221(16) | 0.89683(10) | 0.0577(4) | Uani | d | — |

TABLE 4-continued

Atomic coordinates for the Form II polymorph at 300K.

| Label | Type | x | y | z | U | (a) | (b) | (c) |
|---|---|---|---|---|---|---|---|---|
| N3 | N | 0.43452(13) | 0.47700(14) | 0.86180(9) | 0.0494(4) | Uani | d | — |
| N4 | N | 0.71016(16) | 0.4436(2) | 0.66020(13) | 0.0769(6) | Uani | d | — |
| C1 | C | 0.34001(17) | 0.5217(2) | 0.94483(12) | 0.0577(5) | Uani | d | — |
| H1A | H | 0.300490 | 0.568007 | 0.975832 | 0.069 | Uiso | calc | R |
| C2 | C | 0.38573(15) | 0.58591(19) | 0.89052(11) | 0.0497(4) | Uani | d | — |
| C3 | C | 0.38182(15) | 0.73434(18) | 0.86332(11) | 0.0523(4) | Uani | d | — |
| C4 | C | 0.3872(2) | 0.8417(2) | 0.92076(14) | 0.0674(6) | Uani | d | — |
| H4 | H | 0.396709 | 0.819072 | 0.976025 | 0.081 | Uiso | calc | R |
| C5 | C | 0.3785(2) | 0.9821(2) | 0.89562(17) | 0.0790(7) | Uani | d | — |
| H5 | H | 0.381632 | 1.053508 | 0.934137 | 0.095 | Uiso | calc | R |
| C6 | C | 0.3654(2) | 1.0169(2) | 0.81460(17) | 0.0763(7) | Uani | d | — |
| H6 | H | 0.359869 | 1.111548 | 0.798328 | 0.092 | Uiso | calc | R |
| C7 | C | 0.36027(19) | 0.9119(2) | 0.75739(15) | 0.0691(6) | Uani | d | — |
| H7 | H | 0.351492 | 0.935593 | 0.702381 | 0.083 | Uiso | calc | R |
| C8 | C | 0.36814(17) | 0.7712(2) | 0.78128(12) | 0.0590(5) | Uani | d | — |
| H8 | H | 0.364266 | 0.700640 | 0.742151 | 0.071 | Uiso | calc | R |
| C9 | C | 0.50559(16) | 0.47781(18) | 0.80913(11) | 0.0501(4) | Uani | d | — |
| C10 | C | 0.46955(16) | 0.40069(19) | 0.73576(12) | 0.0529(4) | Uani | d | — |
| H10 | H | 0.398014 | 0.353010 | 0.718754 | 0.064 | Uiso | calc | R |
| C11 | C | 0.54272(16) | 0.3960(2) | 0.68789(12) | 0.0560(5) | Uani | d | — |
| C12 | C | 0.53607(19) | 0.3267(2) | 0.61091(14) | 0.0662(5) | Uani | d | — |
| C13 | C | 0.4544(2) | 0.2392(3) | 0.55587(18) | 0.0949(9) | Uani | d | — |
| H13 | H | 0.385972 | 0.213858 | 0.565892 | 0.114 | Uiso | calc | R |
| C14 | C | 0.4756(3) | 0.1900(4) | 0.4858(2) | 0.1225(13) | Uani | d | — |
| H14 | H | 0.420923 | 0.131481 | 0.448130 | 0.147 | Uiso | calc | R |
| C15 | C | 0.5773(3) | 0.2266(4) | 0.4712(2) | 0.1202(12) | Uani | d | — |
| H15 | H | 0.588749 | 0.193355 | 0.422906 | 0.144 | Uiso | calc | R |
| C16 | C | 0.6614(3) | 0.3095(3) | 0.52453(19) | 0.0972(9) | Uani | d | — |
| H16 | H | 0.730326 | 0.331578 | 0.514281 | 0.117 | Uiso | calc | R |
| C17 | C | 0.6402(2) | 0.3602(3) | 0.59551(15) | 0.0738(6) | Uani | d | — |
| C18 | C | 0.8258(2) | 0.5013(3) | 0.66697(19) | 0.0921(8) | Uani | d | — |
| H18A | H | 0.864807 | 0.436764 | 0.640359 | 0.111 | Uiso | calc | R |
| H18B | H | 0.873649 | 0.509081 | 0.725601 | 0.111 | Uiso | calc | R |
| C19 | C | 0.8153(3) | 0.6420(4) | 0.6271(2) | 0.1155(11) | Uani | d | — |
| H19A | H | 0.768089 | 0.634486 | 0.569068 | 0.173 | Uiso | calc | GR |
| H19B | H | 0.892030 | 0.676251 | 0.631858 | 0.173 | Uiso | calc | GR |
| H19C | H | 0.778915 | 0.706830 | 0.654568 | 0.173 | Uiso | calc | GR |
| C20 | C | 0.65197(18) | 0.4681(2) | 0.71602(14) | 0.0641(5) | Uani | d | — |
| C21 | C | 0.68559(19) | 0.5475(3) | 0.78891(14) | 0.0712(6) | Uani | d | — |
| H21 | H | 0.756336 | 0.596884 | 0.806094 | 0.085 | Uiso | calc | R |
| C22 | C | 0.61138(18) | 0.5516(2) | 0.83551(13) | 0.0620(5) | Uani | d | — |
| H22 | H | 0.632300 | 0.604111 | 0.884799 | 0.074 | Uiso | calc | R |

Example 7. PXRD of the Form I Polymorph

Figure 7:
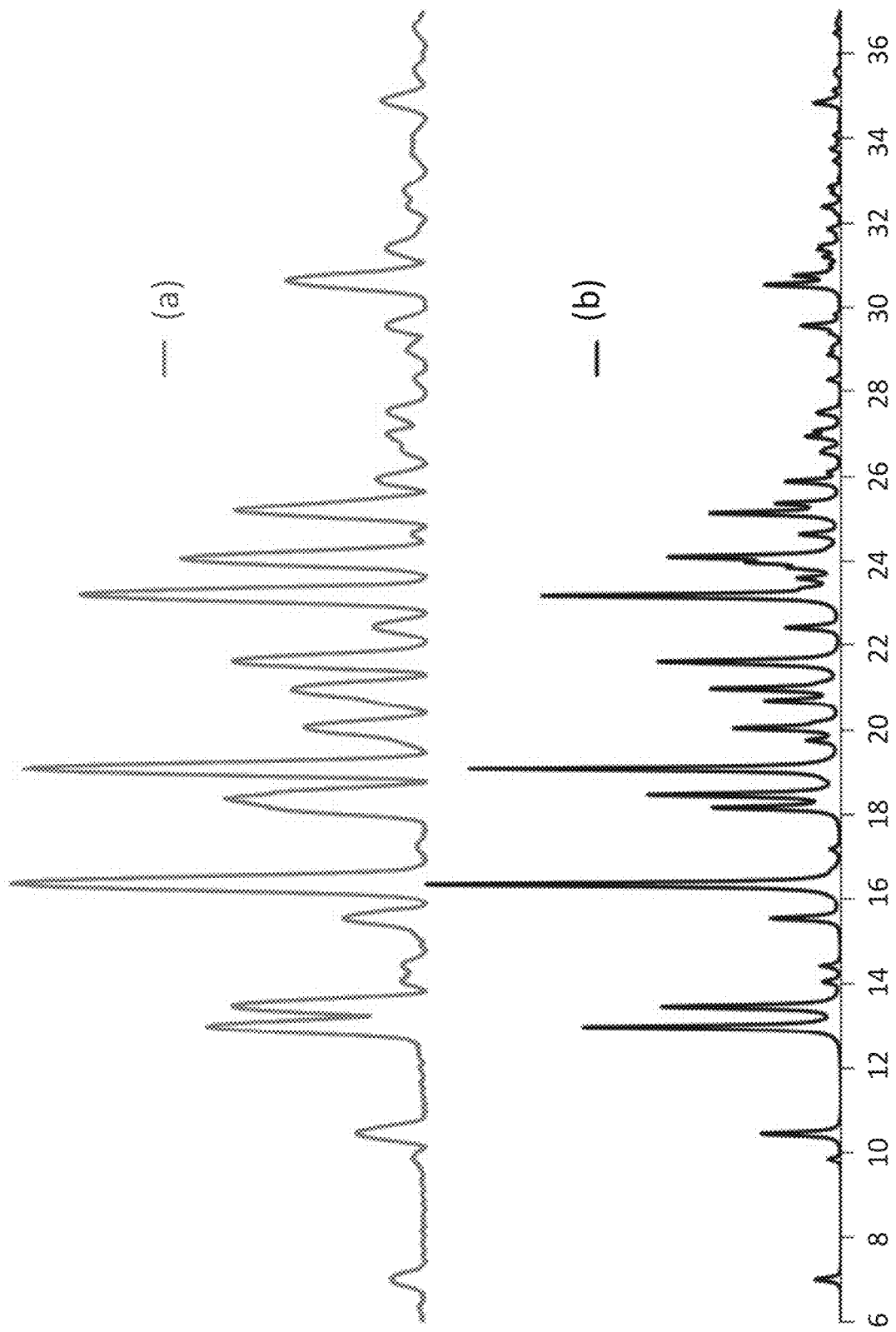
FIG. 7 shows (a) experimental and (b) simulated PXRD diffractograms of the Form I polymorph at 300 K. Horizontal axis=2-theta (°).

The X-ray diffractogram was obtained at 300 K for the Form I polymorph from Example 1 (FIG. 7) and compared to the predicted peaks from the Form I structure at 300 K from Example 5. Good agreement was observed for peak positions and intensities (Table 5).

TABLE 5

Experimental (left) and simulated (right) PXRD pattern peak positions (°) and relative intensities (%) of the Form I polymorph at 300K.

| experimental | | simulated | |
|---|---|---|---|
| 2θ | I/I₀ | 2θ | I/I₀ |
| 7.04 | 8.42 | 7.00 | 6.30 |
| 9.87 | 3.44 | 9.84 | 3.30 |
| 10.49 | 16.83 | 10.44 | 19.09 |
| 12.98 | 52.71 | 12.97 | 62.06 |
| 13.47 | 46.48 | 13.45 | 43.26 |
| 14.04 | 6.16 | 14.03 | 4.52 |
| 14.42 | 5.80 | 14.42 | 5.16 |
| 15.53 | 20.04 | 15.53 | 17.09 |
| 16.36 | 100.00 | 16.35 | 100.00 |
| | | 18.16 | 31.02 |
| 18.37 | 48.54 | 18.46 | 46.63 |
| 19.07 | 96.89 | 19.08 | 89.53 |
| 20.04 | 29.23 | 20.04 | 26.04 |
| | | 20.70 | 18.35 |
| 20.93 | 32.40 | 20.98 | 31.54 |
| 21.61 | 46.64 | 21.61 | 44.08 |
| 22.41 | 12.70 | 22.43 | 13.31 |
| 23.18 | 83.02 | 23.17 | 72.05 |
| 24.06 | 59.04 | 24.10 | 41.66 |
| 24.35 | 6.69 | 24.62 | 10.03 |
| 25.20 | 46.08 | 25.11 | 31.66 |
| | | 25.36 | 15.96 |
| 25.93 | 12.11 | 25.88 | 13.54 |
| 27.55 | 9.50 | | |
| 29.56 | 9.72 | 29.55 | 9.54 |
| 30.62 | 33.40 | 30.53 | 18.54 |
| 31.40 | 9.78 | | |
| | | 30.74 | 11.57 |
| 34.88 | 25.70 | 34.84 | 6.75 |

Figure 8:
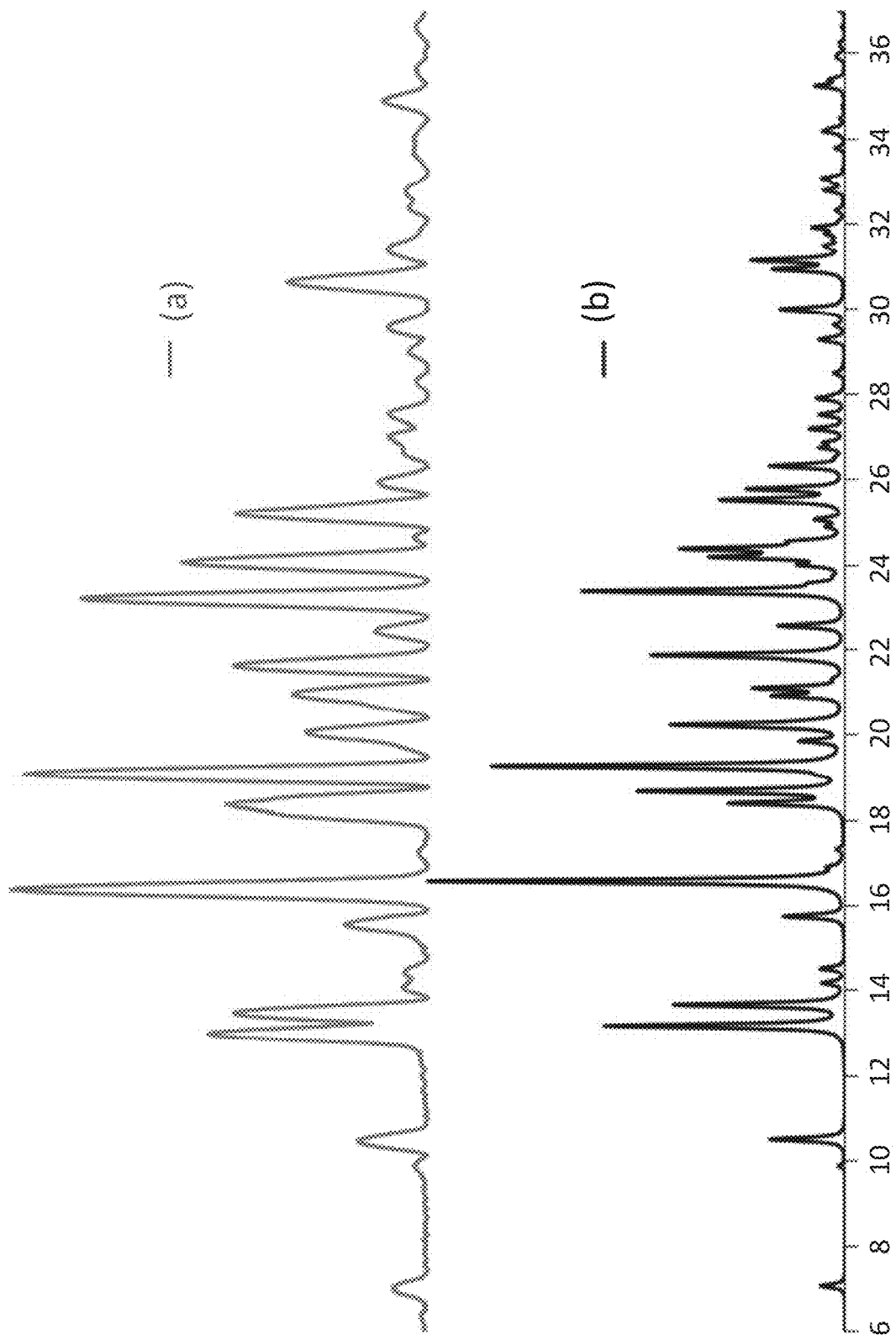
FIG. 8 shows (a) experimental and (b) simulated PXRD diffractograms of the Form I polymorph at 100 K. Horizontal axis=2-theta (°).

The X-ray diffractogram was also obtained at 100 K for the Form I polymorph from Example 1 (FIG. 8) The predicted peaks from the Form I structure at 100 K from Example 5 are disclosed in Table 6.

TABLE 6

Simulated PXRD pattern peak positions (°) and relative intensities (%) of the Form I polymorph at 100K.

| 2θ | I/I$_0$ |
|---|---|
| 7.07 | 7.03 |
| 9.89 | 1.96 |
| 10.50 | 21.26 |
| 13.17 | 68.26 |
| 13.66 | 48.71 |
| 14.16 | 6.56 |
| 14.52 | 7.03 |
| 15.73 | 17.59 |
| 16.57 | 0.20 |
| 18.40 | 33.13 |
| 18.68 | 58.81 |
| 19.27 | 100.00 |
| 20.23 | 49.37 |
| 20.92 | 20.70 |
| 21.10 | 26.29 |
| 21.86 | 55.01 |
| 22.56 | 18.96 |
| 23.37 | 74.52 |
| 24.18 | 38.74 |
| 24.37 | 46.89 |
| 25.52 | 35.64 |
| 25.77 | 27.76 |
| 26.31 | 21.34 |
| 29.99 | 18.08 |
| 30.93 | 20.64 |
| 31.14 | 26.77 |
| 35.24 | 8.58 |

Example 8. PXRD of the Form II Polymorph

Figure 9:
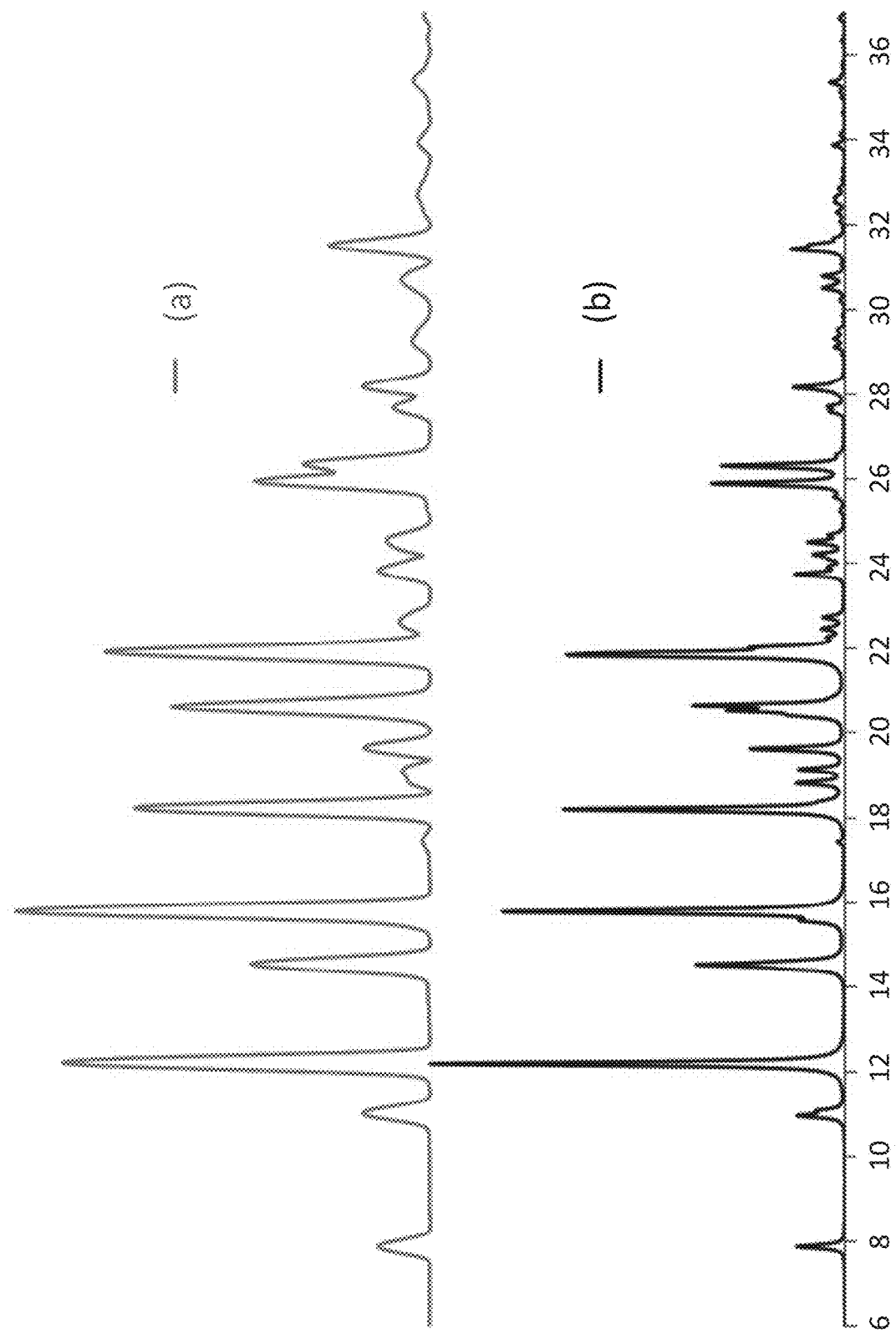
FIG. 9 shows (a) experimental and (b) simulated PXRD diffractograms of the Form II polymorph at 300 K. Horizontal axis=2-theta (°).

The X-ray diffractogram was obtained at 300 K for the Form II polymorph from Example 2 (FIG. 9), and compared to the predicted peaks from the Form I structure at 300 K from Example 6. Good agreement was observed for peak positions and intensities (Table 7).

TABLE 7

Experimental (left) and simulated (right) PXRD pattern peak positions (°) and relative intensities (%) of the Form II polymorph at 300K.

| experimental | | simulated | |
|---|---|---|---|
| 2θ | I/I$_0$ | 2θ | I/I$_0$ |
| 7.87 | 12.63 | 7.86 | 11.55 |
| 11.00 | 16.30 | 10.96 | 11.59 |
| 12.20 | 88.51 | 12.18 | 100.00 |
| 14.54 | 43.23 | 14.53 | 35.94 |
| 15.78 | 100.00 | 15.77 | 82.57 |
| 18.22 | 71.29 | 18.19 | 67.90 |
| | | 18.81 | 11.79 |
| 19.14 | 6.52 | 19.13 | 11.13 |
| 19.67 | 15.87 | 19.62 | 22.87 |
| 20.61 | 62.51 | 20.65 | 36.71 |
| 21.90 | 78.40 | 21.83 | 67.15 |
| 22.65 | 7.55 | 22.73 | 5.28 |
| 23.83 | 12.56 | 23.75 | 12.14 |
| | | 24.21 | 7.71 |
| 24.54 | 10.70 | 24.50 | 8.97 |
| 25.94 | 42.47 | 25.88 | 32.05 |
| 26.32 | 30.44 | 26.30 | 29.71 |
| 27.67 | 8.92 | 27.70 | 4.33 |

TABLE 7-continued

Experimental (left) and simulated (right) PXRD pattern peak positions (°) and relative intensities (%) of the Form II polymorph at 300K.

| experimental | | simulated | |
|---|---|---|---|
| 2θ | I/I$_0$ | 2θ | I/I$_0$ |
| 28.17 | 16.33 | 28.15 | 12.46 |
| 30.69 | 7.01 | 30.50 | 5.40 |
| | | 30.77 | 5.31 |
| 31.49 | 24.28 | 31.42 | 12.98 |

Figure 10:
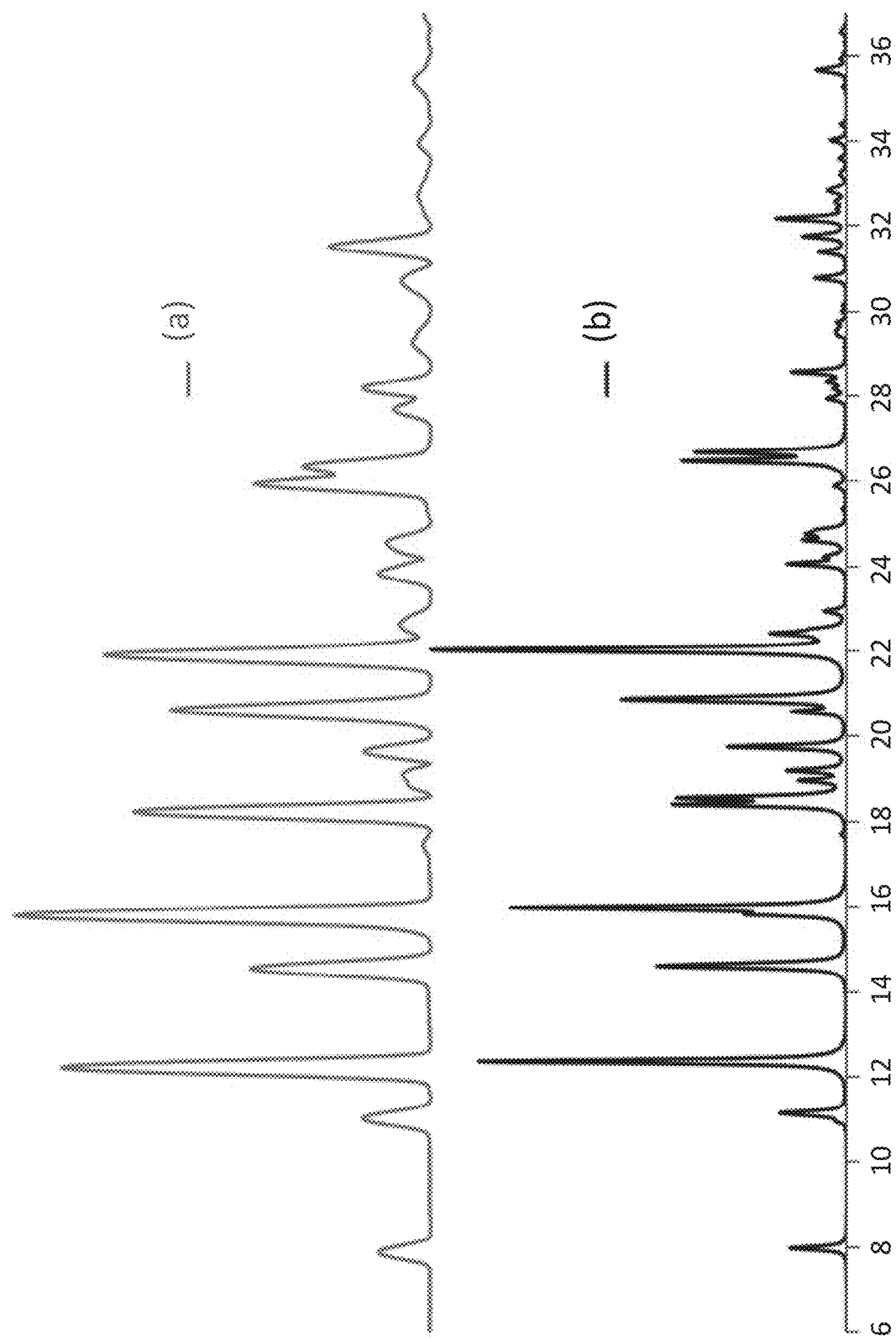
FIG. 10 shows (a) experimental and (b) simulated PXRD diffractograms of the Form II polymorph at 100 K. Horizontal axis=2-theta (°).

The X-ray diffractogram was also obtained at 100 K for the Form II polymorph from Example 1 (FIG. 10) The predicted peaks from the Form II structure at 100 K from Example 5 are disclosed in Table 8.

TABLE 8

Simulated PXRD pattern peak positions (°) and relative intensities (%) of the Form II polymorph at 100K.

| 2θ | I/I$_0$ |
|---|---|
| 7.97 | 13.72 |
| 11.15 | 16.17 |
| 12.35 | 88.44 |
| 14.60 | 45.73 |
| 15.97 | 80.85 |
| 18.39 | 41.91 |
| 18.54 | 40.98 |
| 18.63 | 11.51 |
| 19.20 | 14.53 |
| 19.76 | 28.66 |
| 20.58 | 13.29 |
| 20.87 | 54.09 |
| 22.03 | 100.00 |
| 22.42 | 18.42 |
| 22.94 | 5.63 |
| 24.06 | 14.35 |
| 24.61 | 10.71 |
| 26.48 | 39.71 |
| 26.68 | 36.64 |
| 28.57 | 13.35 |
| 30.77 | 7.66 |
| 31.38 | 6.86 |
| 31.75 | 10.68 |
| 32.17 | 17.00 |

Example 9. FTIR of the Form I and Form II Polymorph

Figure 11:
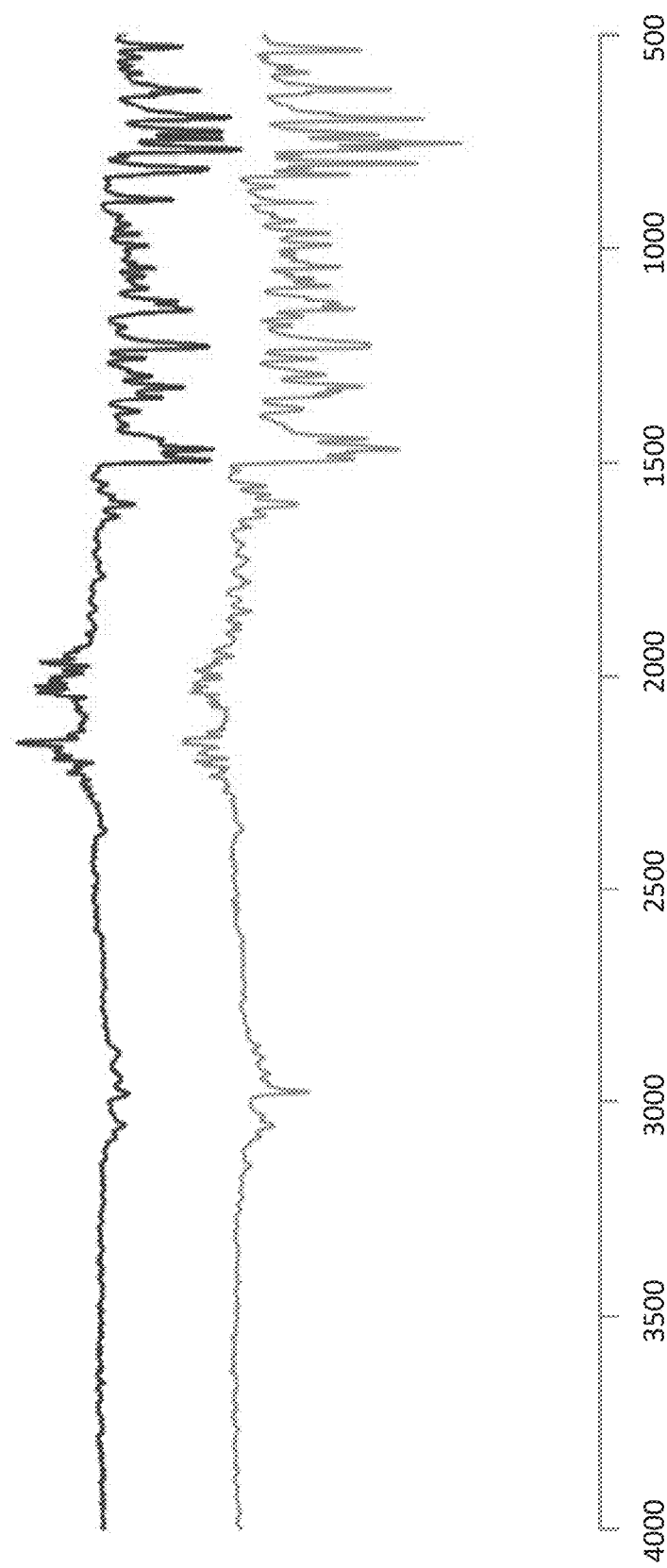
FIG. 11 shows FTIR spectra of (a) the Form I polymorph and (b) the Form II polymorph. Horizontal axis=wave numbers (cm$^{-1}$).

FTIR spectra for the Form I and Form II polymorphs were obtained and are shown in FIG. 11.

Biological Activity Assays

Biological activity for the material disclosed herein can be examined through use of one or more of the following procedures.
Cell Culture
MDA-MB-231, MCF-7 (ATCC), green fluorescent protein (GFP) tagged bone metastatic variant of MDA-MB-435 (GFP-HER2-BM) (from Dr. Danny Welch, The University of Kansas Cancer Center), and MCF10A mammary epithelial cells (ATCC) are cultured and maintained as previously described. MDA-MB-231 and MCF-7 cell lines were obtained in 2000, the MCF-10A cell line was purchased in 2013, and the GFP-HER2-BM cell line was a gift from Dr. Danny Welch in 2008. The cell lines were authenticated by ATCC in 2015.

Rac and Cdc42 Activation Assays

For the $IC_{50}$ curves: Rac1/2/3 and Cdc42 activation is determined, using a G-LISA kit (Cytoskeleton, Inc., Denver, CO). MDA-MB-231 cell lysates is prepared from 24 h MBQ-167 treatment by combining attached and detached cell populations (N=3). Four-parameter dose-response $IC_{50}$ curves are fitted using the non-linear regression function of GraphPad Prism®.

Additionally, Rac, Cdc42, or Rac activation is determined, by pulldowns using the P21-binding domain (PBD) of PAK, or Rho binding domain of Rhotekin. The GTP bound active Rac, Cdc42, or Rho is detected by Western blot (N=3).

Western Blot Analysis

Total cell lysates or pull-downs are Western blotted using routine procedures. The primary antibodies used are: Rac (Rac1,2,3), Cdc42, Bcl-XL, Bcl-2, Mcl-1, PAK1, PAK2, phospho (p)-PAK1(T423)/PAK2(T402), p-PAK1(S199/204)/PAK2(S192/197), p-PAK1(S144/204)/PAK2(S141), LIM kinase (LIMK1), p-LIMK1/2(Tyr507/Thr508), Cofilin, p-cofilin (S3), STAT3, p-STAT3(Y705), p-P-38 MAPK (T180/Y182), p-ERK (T202/Y204), p-Akt (S473), and Akt (Cell Signaling Technology, Inc.) and β-actin (Sigma).

Fluorescence Microscopy

MDA-MB-231 cells were are with vehicle or MBQ-167 at 250 or 500 nM for 24 h. Cells are fixed, permeabilized, and stained with Rhodamine phalloidin to visualize F-actin, and with p-tyrosine or vinculin to visualize focal adhesions. Fluorescence micrographs are acquired at 600× in an Olympus BX40 fluorescence microscope using a Spot digital camera.

Cell Migration Assays

Transwell assay Quiescent MDA-MB-231 cells are treated with vehicle or MBQ-167 (250 nM) for 24 h. The attached and detached populations are separated and exactly $2 \times 10^5$ cells were placed on the top well of Transwell chambers with 5% FBS in the bottom well. The number of cells that migrated to the underside of the membrane following a 7 h incubation is quantified after staining fixed cells with propidium iodide (PI). For each treatment (N=3), cells in 20 microscopic fields are quantified.

Wound healing scratch assay MDA-MB-231 cells plated on 6-well plates at equal cell density are incubated in 10% FBS until confluent. The media is changed to 2% FBS and a single scratch is made in the center of the monolayer culture with a pipet tip. MBQ-167 is added at 0, 250, or 500 nM immediately following wounding. Images are digitally acquired from an Olympus microscope (4× magnification) at 0, 8, 12, and 24 h and the scratch distance is quantified in Adobe Photoshop. N=3 biological replicates (with 2 technical replicates each).

Mammosphere Formation Assay

Equal numbers of MDA-MB-231 cells treated with vehicle or MBQ-167 are seeded in ultra-low attachment plates (Corning) at a density of 500 cells/well in serum-free mammary epithelium basal medium (Lonza). Mammospheres are counted after 4 days incubation in 0 or 250 nM MBQ-167 at 37° C., 5% $CO_2$. Mammosphere-forming efficiency is calculated as the number of mammospheres divided by the number of cells seeded per well and expressed relative to vehicle controls.

Cell Viability Assays

Equal numbers of MDA-MB-231, GFP-HER2-BM, or MCF-10A cells are incubated in 0-1 µM MBQ-167 for 120 h. The CellTiter 96® Non-Radioactive Cell Proliferation Assay (Promega, Fitchburg, WI) is used according to the manufacturer's instructions. This assay allows the quantification of the viability of both attached and detached cells in the same well. GIso is determined as $100 \times (T-T_0)/(C-T_0)=50$ (T=the optical density of drug treatment after 120 h. $T_0$=the optical density at time zero, and C=the optical density of the untreated cells). Curves are fitted using the four-parameter logistic nonlinear regression models in GraphPad Prism software.

Cell Cycle Progression

MDA-MB-231 cells are incubated with 0 or 250 nM MBQ-167 for 48 h and all cells (detached and attached) are stained with PI. Cell cycle stage is analyzed using a four-color flow cytometer (FACSCalibur, BD Biosciences, San Jose, CA). A total of 20,000 events are analyzed for each sample. List-mode files are collected using Cell Quest software 3.3 and analyzed using the Flow Jo software vX.0.7 (BD Biosciences, San Jose, CA).

Apoptosis Assay

Apoptosis is measured using a Caspase-Glo3/7 Luminescence Assay Kit as per manufacturer's instructions (Promega, Corp., Madison, WI, USA). Following treatment of equal numbers of cells with vehicle or MBQ-167 for 24 h, Caspase-3/7 Glo reagent is added and incubated at room temperature for 60 min. Caspase-3/7 activities are determined by quantifying luminescence.

Annexin V Staining

Apoptotic cells are detected by fluorescence microscopy of Annexin V-Cy3-18 stained cells as per manufacturer's instructions (Sigma-Aldrich, St Louis, MO, USA). Briefly, GFP-MDA-MB-231 cells grown on coverslips are treated with vehicle, or 250 or 500 nM MBQ-167 for 6 h and stained with Annexin V-Cy3-18 in binding buffer (10 mM HEPES/NaOH, pH 7.5, 0.14 M NaCl, 2.5 mM $CaCl_2$) for 15 min at room temperature. Coverslips are washed in binding buffer and fixed with 3.7% paraformaldehyde prior to fluorescence microscopy. Images are digitally acquired from an Olympus inverted fluorescence microscope.

Animal Protocol

All animal studies are conducted under approved protocol #A8180112 Institutional Animal Care and Use Committee, in accordance with the *NIH Guideline for the Care and Use of Laboratory Animals*. Female athymic nu/nu mice and severe combined immunodeficiency Crl:SHO-Prkdc SCID Hairless 4 to 5 wk old (Charles River Laboratories, Inc., Wilmington, MA) are maintained under pathogen-free conditions in HEPA-filtered cages.

Tumor Establishment

GFP-HER2-BM cells ($\sim 5 \times 10^5$) or GFP-MDA-MB-231 cells ($1 \times 10^5$) in Matrigel (BD Biosciences, San Jose, CA) are injected at the fourth right mammary fat pad under isofluorane inhalation (1-3% in oxygen using an inhalation chamber at 2 L/min) to produce orthotopic primary tumors. After tumor establishment (1 wk post-inoculation), animals are randomly divided into treatment groups (n=6).

Administration of MBQ-167

Mice are treated with vehicle (12.5% ethanol, 12.5% Cremophor (Sigma-Aldrich, St. Louis, MO), and 75% 1×PBS pH 7.4), or 1 or 10 mg/kg BW MBQ-167 by i.p. injection in a 100 µL volume 3× a wk. Treatments are continued until sacrifice at day 65.

Whole Body Fluorescence Image Analysis

Mammary tumor growth is quantified as changes in the integrated density of GFP fluorescence. Mice are imaged on day 1 of treatment administration, and once a week thereafter for 65 days, using the FluorVivo small animal in vivo imaging system (INDEC Systems, Inc., Santa Clara, CA). Tumor fluorescence intensities are analyzed using Image J software (National Institutes of Health, Bethesda, MD). Relative tumor growth is calculated as the integrated density of fluorescence of each tumor on each day of imaging relative to the integrated density of fluorescence of the same tumor on day 1 of treatment. Optimal Tumor growth is calculated as % T/C=(δT/δC)×100 when δT>0, δT=average tumor size on day 65 of treated mice-average tumor size on day 01 of treated mice. δC=average tumor size on day 65 of control mice-average tumor size on day 01 of control mice. Tumor growth delay is calculated as the percentage by which the treated group tumor size is delayed in attaining a specified number of doublings (from day 1) compared with controls using: [(T−C)/C]×100, where T and C are the median times in days for treated and control groups to double in tumor size.

Analysis of Metastases

Following sacrifice, lungs, kidneys, livers, bones, and spleens are excised and immediately stored in liquid $N_2$. Stored organs are thawed and analyzed by fluorescence microscopy, as described.

Liver Enzyme Assays

Frozen stored livers are thawed and homogenized to measure alkaline phosphatase (ALP) and alanine transaminase (ALT) activities using colorimetric assay kits from Abcam and Cayman Chemicals respectively, as per manufacturer's instructions.

Statistical Analysis

Statistical analyses use Microsoft Excel and GraphPad Prism, and differences are considered statistically significant at P≤0.05.

All references, patents or applications, U.S. or foreign, cited in the application are hereby incorporated by reference as if written herein in their entireties. Where any inconsistencies arise, material literally disclosed herein controls.

From the foregoing description, one skilled in the art can easily ascertain the essential characteristics of this disclosure, and without departing from the spirit and scope thereof, can make various changes and modifications of the disclosure to adapt it to various usages and conditions.

What is claimed is:

1. Polymorph I of the crystalline form of the compound 9-ethyl-3-(5-phenyl-1H-1,2,3-triazol-1-yl)-9H-carbazole:

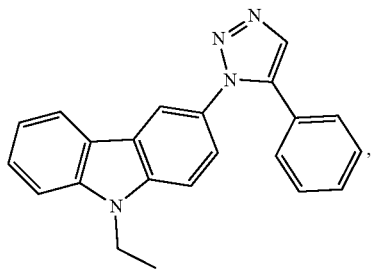 [SMILES: CCn1c2ccccc2c2cc(-n3nncc3-c3ccccc3)ccc21]

wherein said polymorph has three or more powder x-ray diffraction (PXRD) peaks chosen from about 12.98, about 13.47, about 16.36, about 18.37, about 19.07, about 21.61, about 23.18, about 24.06, about 25.20, and about 30.62 degrees 2-theta.

2. A pharmaceutical composition comprising a compound as recited in claim 1 together with a pharmaceutically acceptable carrier.

3. A method of treatment of a RhoGTPase-mediated disease comprising the administration of a therapeutically effective amount of a compound as recited in claim 2 to a patient in need thereof.

4. The method as recited in claim 3, wherein the disease is cancer.

5. The method as recited in claim 4, wherein the cancer is selected from the group consisting of breast cancer, pancreatic cancer, ovarian cancer, gastric cancer, and neuronal cancer.

6. The method as recited in claim 5, wherein the cancer is pancreatic cancer.

7. The method as recited in claim 5, wherein the cancer is ovarian cancer.

8. The method as recited in claim 5, wherein the cancer is gastric cancer.

9. The method as recited in claim 5, wherein the cancer is neuronal cancer.

10. The method as recited in claim 5, wherein the cancer is breast cancer.

11. The method of claim 3, wherein the disease is mediated by a GTPase.

12. The method as recited in claim 11, wherein the GTPase is Rac1 or Cdc42.

13. The method as recited in claim 12, wherein the GTPase is Rac 1.

14. The method as recited in claim 12, wherein the GTPase is Cdc42.

15. A method of treatment of a RhoGTPase-mediated disease comprising the administration of:
    (a) a therapeutically effective amount of a compound as recited in claim 1; and
    (b) another therapeutic agent.

* * * * *